US010214731B2

(12) United States Patent
Crystal et al.

(10) Patent No.: US 10,214,731 B2
(45) Date of Patent: Feb. 26, 2019

(54) ADENO-ASSOCIATED VIRUS MEDIATED DELIVERY OF C1E1 AS A THERAPY FOR ANGIOEDEMA

(71) Applicant: Cornell University, Ithaca, NY (US)

(72) Inventors: Ronald G. Crystal, New York, NY (US); Odelya E. Pagovich, New York, NY (US); Maria J. Chiuchiolo, Washington, DC (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/167,729

(22) Filed: May 27, 2016

(65) Prior Publication Data
US 2016/0347822 A1 Dec. 1, 2016

Related U.S. Application Data

(60) Provisional application No. 62/324,183, filed on Apr. 18, 2016, provisional application No. 62/167,603, filed on May 28, 2015.

(51) Int. Cl.
C12N 7/00 (2006.01)
A01K 67/027 (2006.01)
C12N 9/64 (2006.01)
C07K 14/81 (2006.01)
C12N 15/86 (2006.01)

(52) U.S. Cl.
CPC ............ C12N 7/00 (2013.01); A01K 67/0275 (2013.01); C07K 14/8121 (2013.01); C12N 9/6451 (2013.01); C12N 15/86 (2013.01); C12Y 304/21038 (2013.01); A01K 2217/00 (2013.01); A01K 2217/07 (2013.01); A01K 2227/105 (2013.01); A01K 2267/0368 (2013.01); C12N 2750/14141 (2013.01); C12N 2750/14143 (2013.01)

(58) Field of Classification Search
None
See application file for complete search history.

(56) References Cited

U.S. PATENT DOCUMENTS

| | | | |
|---|---|---|---|
| 4,797,368 | A | 1/1989 | Carter et al. |
| 4,863,457 | A | 9/1989 | Lee |
| 5,378,475 | A | 1/1995 | Smith et al. |
| 5,443,505 | A | 8/1995 | Wong et al. |
| 5,464,758 | A | 11/1995 | Gossen et al. |
| 5,814,618 | A | 9/1998 | Bujard et al. |
| 6,342,390 | B1 | 1/2002 | Wiener et al. |
| 6,723,551 | B2 | 4/2004 | Kotin et al. |
| 6,821,511 | B2 | 11/2004 | Kotin et al. |
| 7,112,715 | B2 | 9/2006 | Chambon et al. |
| 2003/0073652 | A1 | 4/2003 | Pollard et al. |
| 2003/0140358 | A1 | 7/2003 | Nuijens et al. |
| 2014/0228300 | A1 | 8/2014 | Bhattacharjee et al. |

FOREIGN PATENT DOCUMENTS

| | | |
|---|---|---|
| EP | 1598428 A1 | 11/2005 |
| WO | WO 2014/113701 A1 | 7/2014 |
| WO | WO 2015/035190 A1 | 3/2015 |

OTHER PUBLICATIONS

Davis-Lorton M. J Drugs Dermatol. Feb. 2015;14(2):151-7.*
Aberer, "Hereditary angioedema treatment options: The availability of new therapies", *Annals of Medicine*, 44: 523-529 (2012).
Ausubel et al., *Current Protocols in Molecular Biology*, Greene Publishing Associates and John Wiley & Sons, NY, (1994) (Table of Contents only).
Aygoren-Pursun et al., "Socioeconomic burden of hereditary angioedema: results from the hereditary angioedema burden of illness study in Europe", *Orphanet Journal of Rare Diseases*, 9: 1-9 (2014).
Banerji, "The burden of illness in patients with hereditary angioedema", *Ann Allergy Asthma Immunol.*, 111: 329-336 (2013).
Bantel-Schaal et al., Human Adeno-Associated Virus Type 5 Is Only Distantly Related to Other Known Primate Helper-Dependent Parvoviruses, *Journal Of Virology*, 73(2): 939-947 (1999).
Bork et al., "Benefits and risks of danazol in hereditary angioedema: a long-term survey of 118 patients"*Ann. Allergy Asthma Immunol.*, 100: 153-161 (2008).
Bowen et al., "Hereditary angioderna: a current state-of-the-art review, VII: Canadian Hungarian 2007 International Consensus Algorithm for the Diagnosis, Therapy, and Management of Hereditary Angioedema", *Ann Allergy Asthma Immunol*,100 (Suppl. 2): S30-S40 (2008).
Carter, Adeno-Associated Virus Vectors in Clinical Trials, *Human Gene Therapy*, 16: 541-550 (2005).
Cearley et al., Transduction Characteristics of Adeno-associated Virus Vectors Expressing Cap Serotypes 7, 8, 9, and Rh10 in the Mouse Brain, *Molecular Therapy*, 13(3): 528-537 (2006).
Charignon et al., "Icatibant, the bradykinin B2 receptor antagonist with target to the interconnected kinin systems", *Expert Opinion on Pharmacotherapy*, 13: 15, 2233-2247 (2012).
Chiorini et al., Cloning of Adeno-Associated Virus Type 4 (AAV4) and Generation of Recombinant AAV4 Particles, *Journal Of Virology*, 71(9): 6823-6833 (1997).
Chiorini et al., Cloning and Characterization of Adeno-Associated Virus Type 5, *Journal Of Virology*, 73(2): 1309-1319 (1999).
Cicardi et al., Long-term treatment of hereditary angiodema with attenuated androgens: A survey of a 13-year experience, *J Allergy Clin Immunol*, 87(4): 768-773 (1991).

(Continued)

*Primary Examiner* — Qian Janice Li
(74) *Attorney, Agent, or Firm* — Leydig, Voit & Mayer, Ltd.

(57) ABSTRACT

This invention is directed to a vector which comprises a promoter operably linked to a nucleic acid sequence encoding the human C1 esterase inhibitor or Factor XII. The invention is also directed to a composition comprising the vector and a method of using the vector to treat or prevent hereditary angioedema.

14 Claims, 19 Drawing Sheets

(19 of 19 Drawing Sheet(s) Filed in Color)

Specification includes a Sequence Listing.

(56) References Cited

OTHER PUBLICATIONS

Cicardi et al., Side effects of long-term prophylaxis with attenuated androgens in hereditary angioedema: Comparison of treated and untreated patients, *J Allergy Clin Immunol*, 99(2): 194-196 (1997).
Cugno et al., C1-inhibitor deficiency and angioedema: molecular mechanisms and clinical progress, *Trends in Molecular Medicine*, 15(2): 69-78 (2009).
Daly et al., Neonatal gene transfer leads to widespread correction of pathology in a murine model of lysosomal storage disease, *Proc. Natl. Acad. Sci. U.S.A.*, 96: 2296-2300 (1999).
De et al., High Levels of Persistent Expression of A1-Antitrypsin Mediated by the Nonhuman Primate Serotype rh.10 Adeno-associated Virus Despite Preexisting Immunity to Common Human Adeno-associated Viruses, *Molecular Therapy*, 13(1): 67-76 (2006).
De La Cruz et al., Analysis of SERPING1 expression on hereditary angioedema patients: Quantitative analysis of full-length and exon 3 splicing variants, Immunolgy Letters, 141: 158-164 (2011).
Frank, Hereditary Angioedema: The Clinical Syndrome and its Management in the United States, *Immunology and Allergy Clinics of North America*, 26: 653-668 (2006).
Flotte, New AAV Serotypes May Broaden the Therapeutic Pipeline to Human Gene Therapy, *Molecular Therapy*, 13(1): 1-2 (2006).
Fuhrmann-Benzakein et al., Inducible and irreversible control of gene expression using a single transgene, *Nucleic Acids Research*, 28 (23): e99, 1-5 (2000).
Gao et al., Glades of Adeno-Associated Viruses Are Widely Disseminated in Human Tissues, *Journal Of Virology*, 78(12): 6381-6388 (2004).
Gao et al., Novel adeno-associated viruses from rhesus monkeys as vectors for human gene therapy, *Proc. Natl. Acad. Sci. USA*, 99(18): 11854-11859 (2002).
Gao et al., Biology of AAV Serotype Vectors in Liver-Directed Gene Transfer to Nonhuman Primates, *Molecular Therapy*, 13(1): 77-87 (2006).
Goeddel, Systems for Heterologous Gene Expresssion, Gene Expression Technology: *Methods in Enzymology*, 185:3-7, Academic Press, San Diego, CA. (1990).
Gooptu et al., Conformational Pathology of the Serpins: Themes, Variations, and Therapeutic Strategies, *Annual Review of Biochemistry*, 78: 147-176 (2009).
Gower et al., Hereditary Angioedema Caused by C1-Esterase Inhibitor Deficiency: A Literature-Based Analysis and Clinical Commentary on Prophylaxis Treatment Strategies, *World Allergy Organization Journal*, 4: S9-S21 (2011).
Im et al., The AAV Origin Binding Protein Rep68 is an ATP-Dependent Site-Specific Endonuclease with DNA Helicase Activity, *Cell*, 61: 447-457 (1990).
Indra, et al., Temporarily-controlled site-specific mutagenesis in the basal layer of the epidermis: comparison of the recombinase activity of the tamoxifen-inducible Cre-ER$^T$ and Cre-ER$^{T2}$ recombinases, *Nucleic Acids Research*, 27(22): 4324-4327 (1999).
Kramer et al., Transgene Control Engineering in Mammalian Cells, *Methods in Molecular Biology*, 308: 123-144 (2005).
Kreuz et al., C1-inhibitor concentrate for individual replacement therapy in patients with severe hereditary angioedema refractory to danazol prophylaxis, *Transfusion* 49:1987-1995 (2009).
Mao et al., Persistent Suppression of Ocular Neovascularization with Intravitreal Administration of AAVrh.10 Coding for Bevacizumab, *Human Gene Therapy*, 22: 1525-1535 (2011).
Niwa et al., Efficient selection for high-expression transfectants with a novel eukaryotic vector, *Gene*, 108: 193-200 (1991).

No et al., Ecdysone-inducible gene expression in mammalian cells and transgenic mice, *Proc. Natl. Acad. Sci. USA*, 93: 3346-3351 (1996).
Papadopoulou-Alataki, Upper airway considerations in hereditary angioedema, *Current Opinion in Allergy and Clinical Immunology*, 10:20-25 (2010).
Parikh et al., New Therapeutics in C1INH Deficiency: A Review of Recent Studies and Advances, *Curr. Allergy Asthma Rep.*, 11: 300-308 (2011).
Pereira et al., The Adeno-Associated Virus (AAV) Rep Protein Acts as both a Repressor and an Activator To Regulate AAV Transcription during a Productive Infection, *Journal Of Virology*, 71(2): 1079-1088 (1997).
Remington, The Science and Practice of Pharmacy, 21st Edition, Lippincott Williams & Wilkins, Philadelphia, PA (2001) (Table of Contents only).
Rutledge et al., Infectious Clones and Vectors Derived from Adeno-Associated Virus (AAV) Serotypes Other Than AAV Type 2, *Journal Of Virology*, 72(1): 309-319 (1998).
Sambrook et al., Molecular Cloning: A Laboratory Manual, Fourth Edition, Cold Spring Harbor Press, Cold Spring Harbor, NY, (2001) (Table of Contents only).
Sondhi et al., Enhanced Survival of the LINCL Mouse Following CLN2 Gene Transfer Using the rh.10 Rhesus Macaque-derived Adeno-associated Virus Vector, *Molecular Therapy*, 15(3): 481-491 (2007).
Srivastava et al., Nucleotide Sequence and Organization of the Adeno-Associated Virus 2 Genome, *Journal of Virology*, 45(2): 555-564 (1983).
Tourangeau et al., The New Era of C1-Esterase Inhibitor Deficiency Therapy, *Curr. Allergy Asthma Rep.*, 11: 345-351 (2011).
Watanabe et al., AAVrh.10-mediated genetic delivery of bevacizumab to the pleura to provide local anti-VEGF to suppress growth of metastatic lung tumors, *Gene Therapy*, 17(8): 1042-1051 (2010).
Wright et al., Recombinant adeno-associated virus: Formulation challenges and strategies for a gene therapy vector, *Current Opinion in Drug Discovery & Development*, 6(2): 174-178 (2003).
Wright et al., Identification of Factors that Contribute to Recombinant AAV2 Particle Aggregation and Methods to Prevent Its Occurrence during Vector Purification and Formulation, *Molecular Therapy*, 12(1): 171-178 (2005).
Wu et al., Adeno-associated Virus Serotypes: Vector Toolkit for Human Gene Therapy, *Molecular Therapy*, 14(3): 316-327 (2006).
Wu et al., Mutational Analysis of the Adeno-Associated Virus Type 2 (AAV2) Capsid Gene and Construction of AAV2 Vectors with Altered Tropism, *Journal Of Virology*, 74(18): 8635-8647 (2000).
Zuraw et al., US Hereditary Angioedema Association Medical Advisory Board 2013 Recommendations for the Management of Hereditary Angioedema Due to C1 Inhibitor Deficiency, *J. Allergy Clin. Immunol. Pract.*, 1(5): 458-467 (2013).
GenBank Accession Record No. U89790.1, submitted on Feb. 17, 1997.
GenBank Accession Record No. J01901.
GenBank Accession Record No. AF043303.1.
GenBank Accession Record No. AF085716.1.
WIPO, PCT International Search Report in Application No. PCT/US2016/034852, dated Aug. 29, 2016, 4 pages.
European Patent Office, extended European Search Report in Application No. 16800841.5 (dated Jul. 25, 2018).
Bracho, Hereditary Angioedema, *Current Opinion in Hematology*, 12(6): 493-498 (2005).
European Patent Office, partial supplementary European search report in Application No. 16800841.5 (dated Apr. 19, 2018).

* cited by examiner

Mouse C1EI (ELISA)

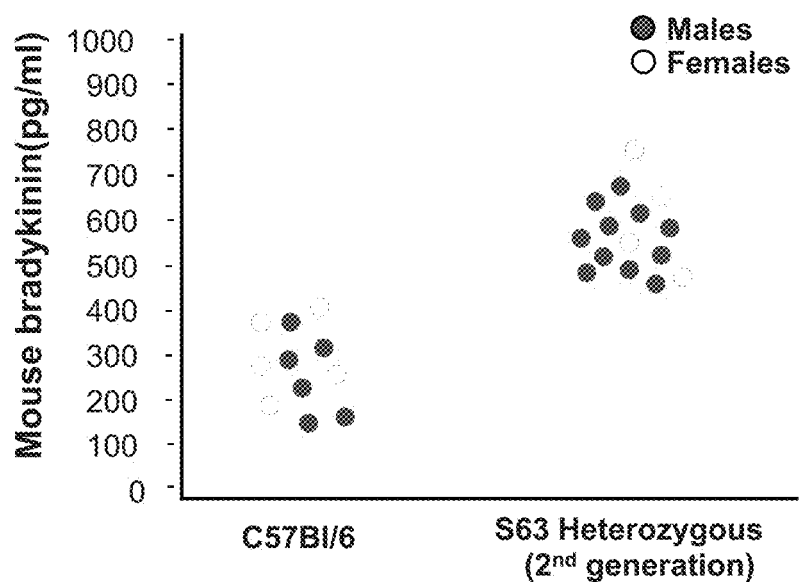

Expression cassette

AAVrh.10hC1EI
AAV8hC1EI
AAV9hC1EI

**AAVrh.10hC1EI *in vitro* directed expression of C1EI**

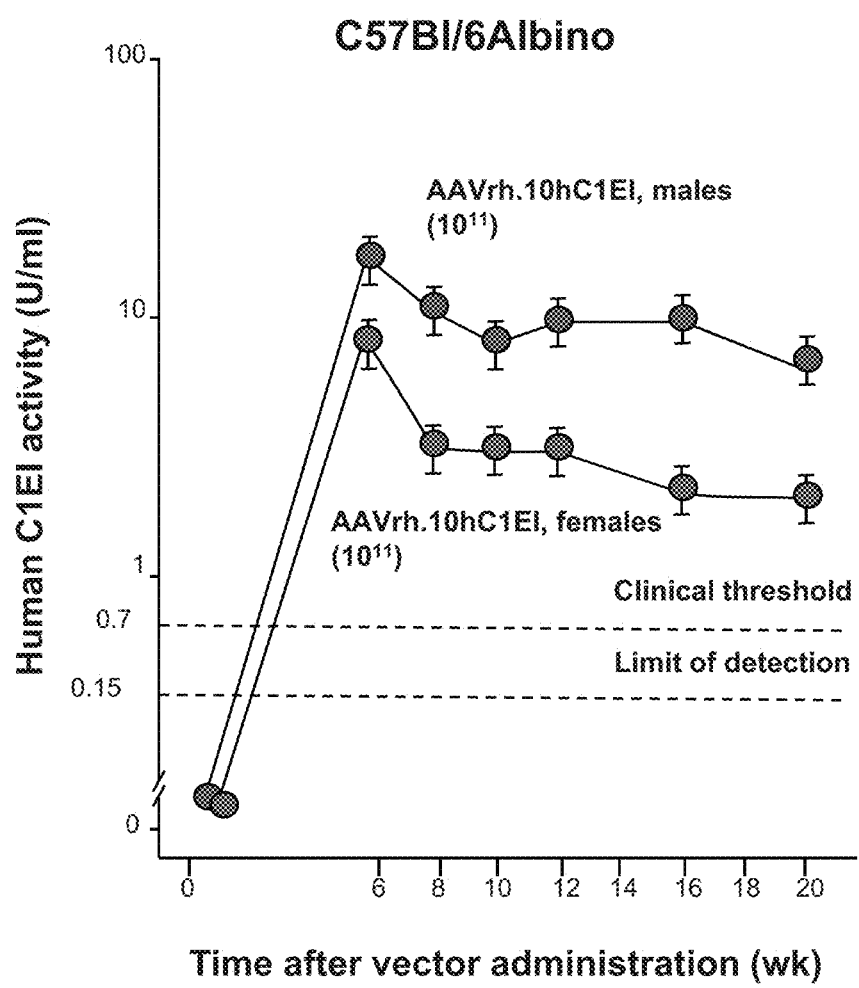

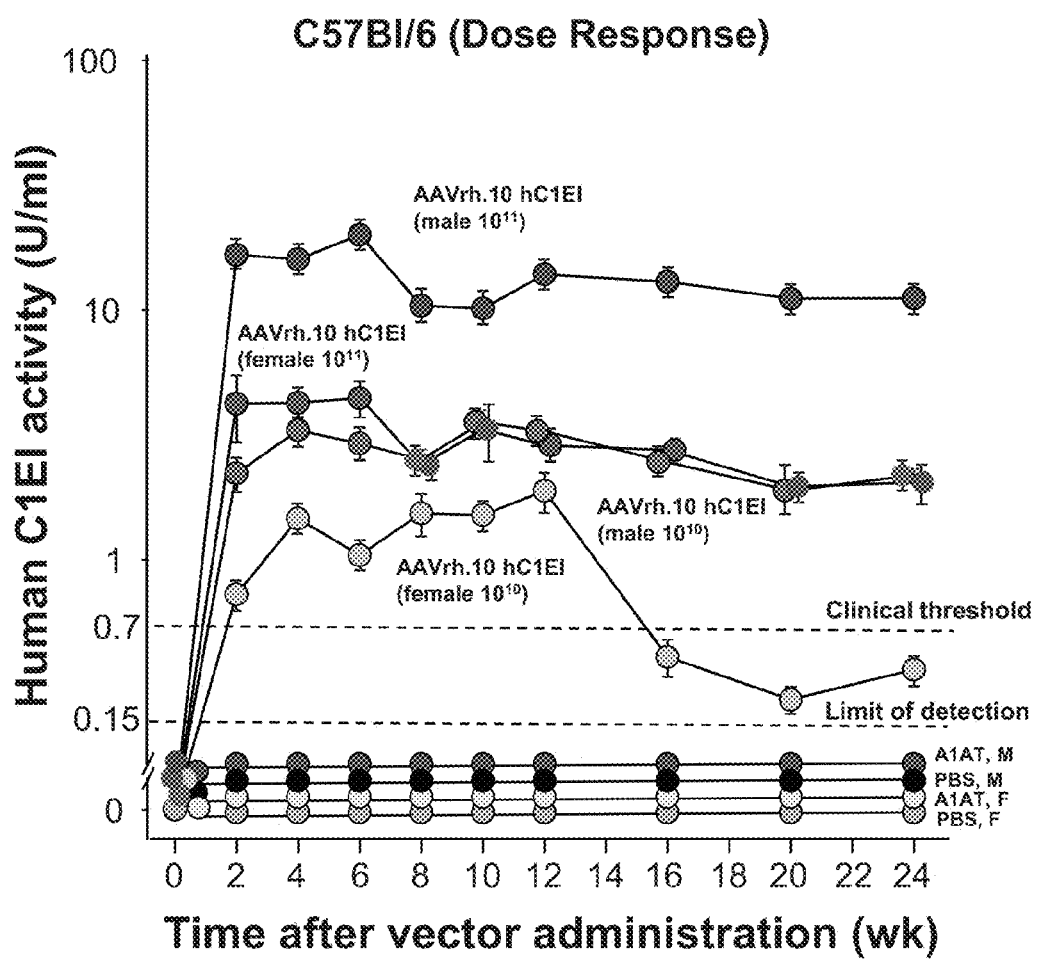

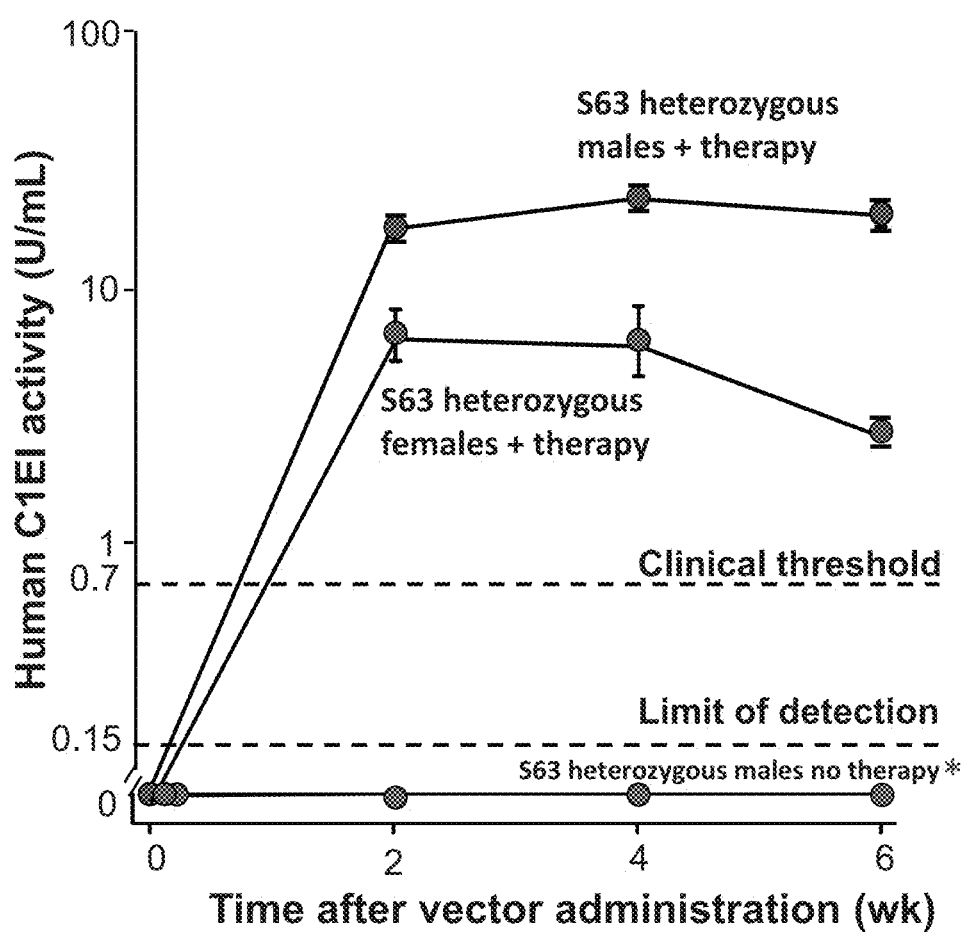
*S63 heterozygous females no therapy n=1, no activity

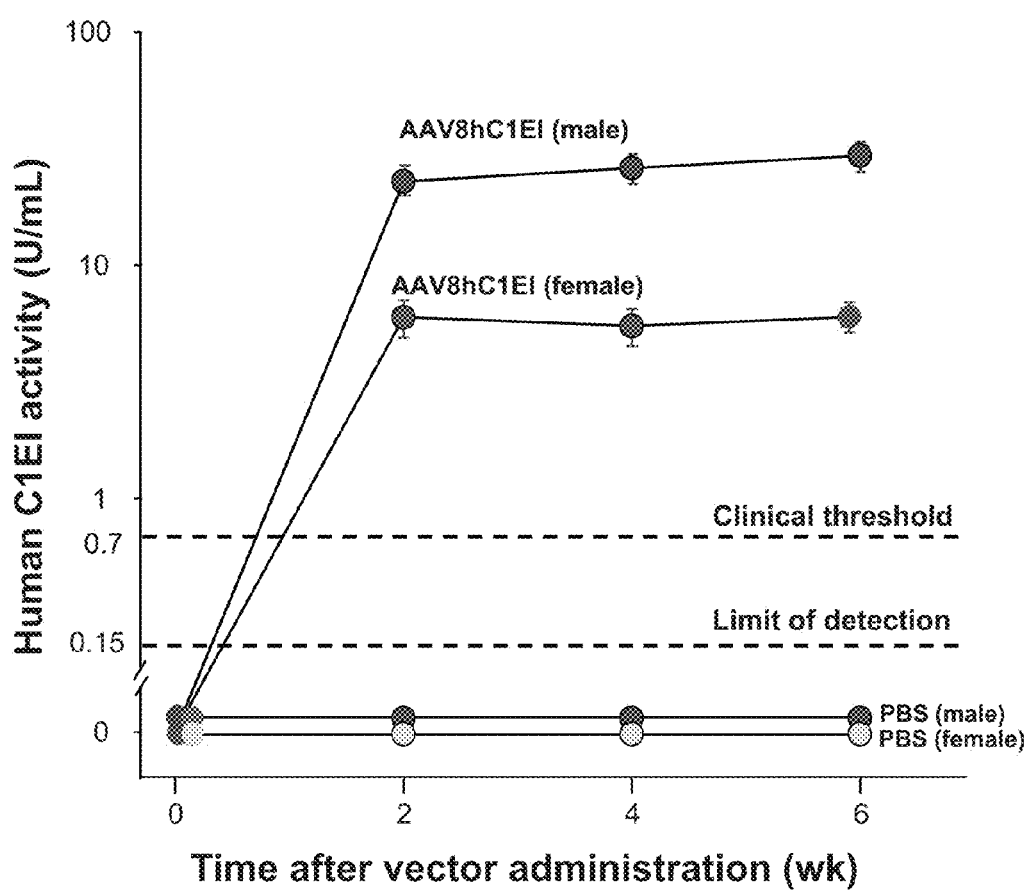

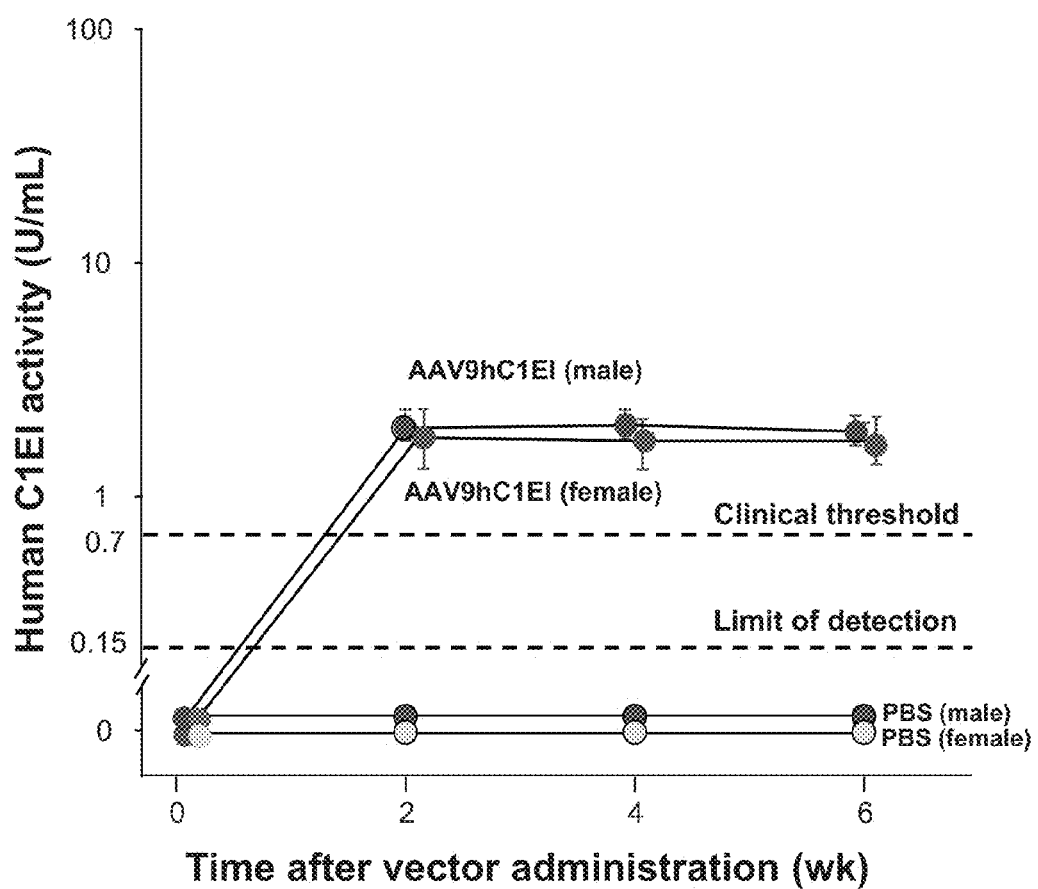

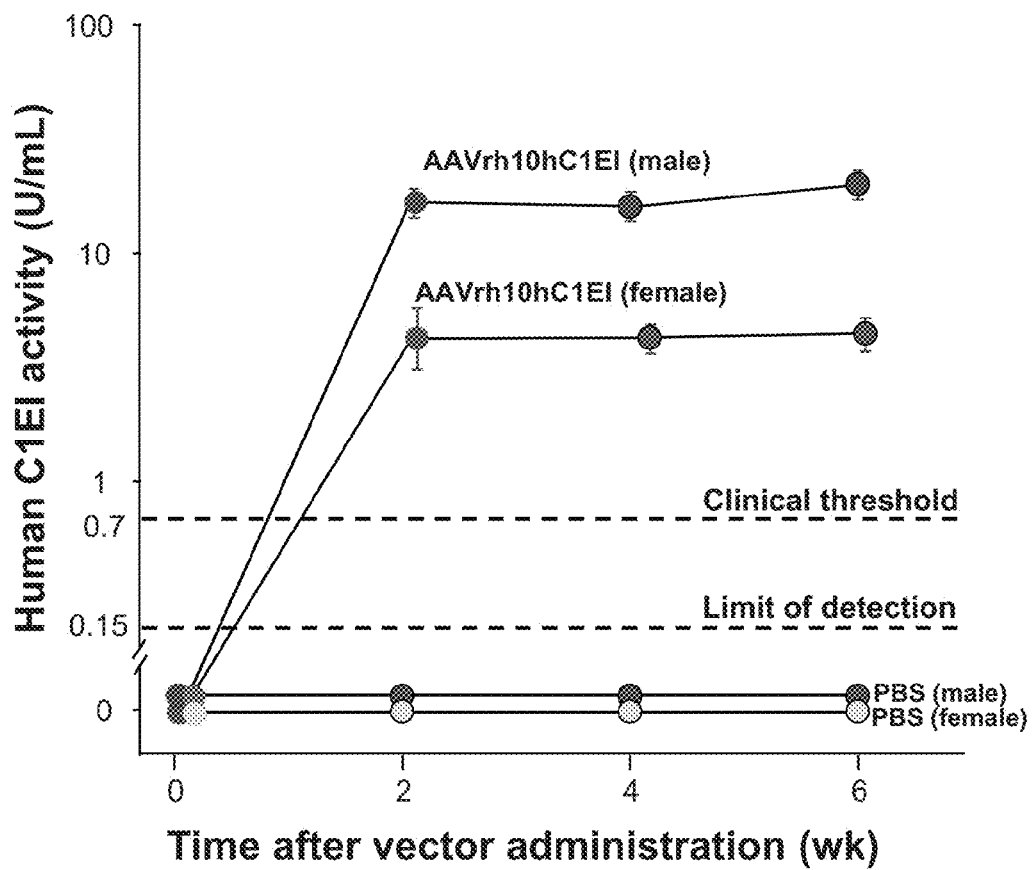

AAV8hC1EI, AAV9hC1EI, or AAVrh.10hC1EI Vector

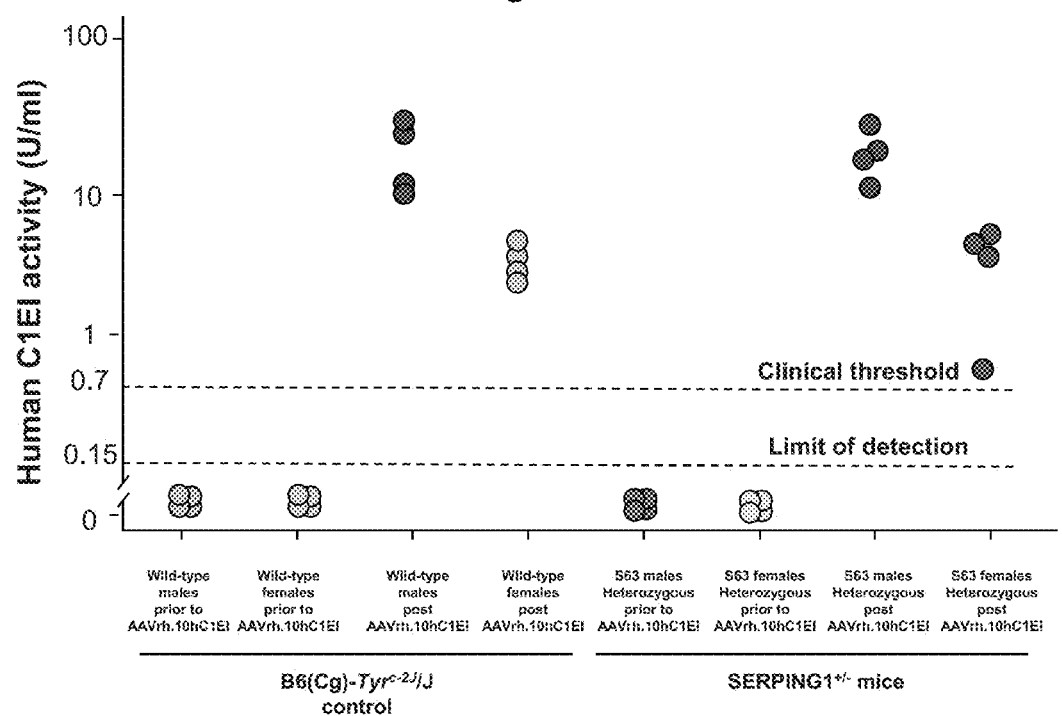

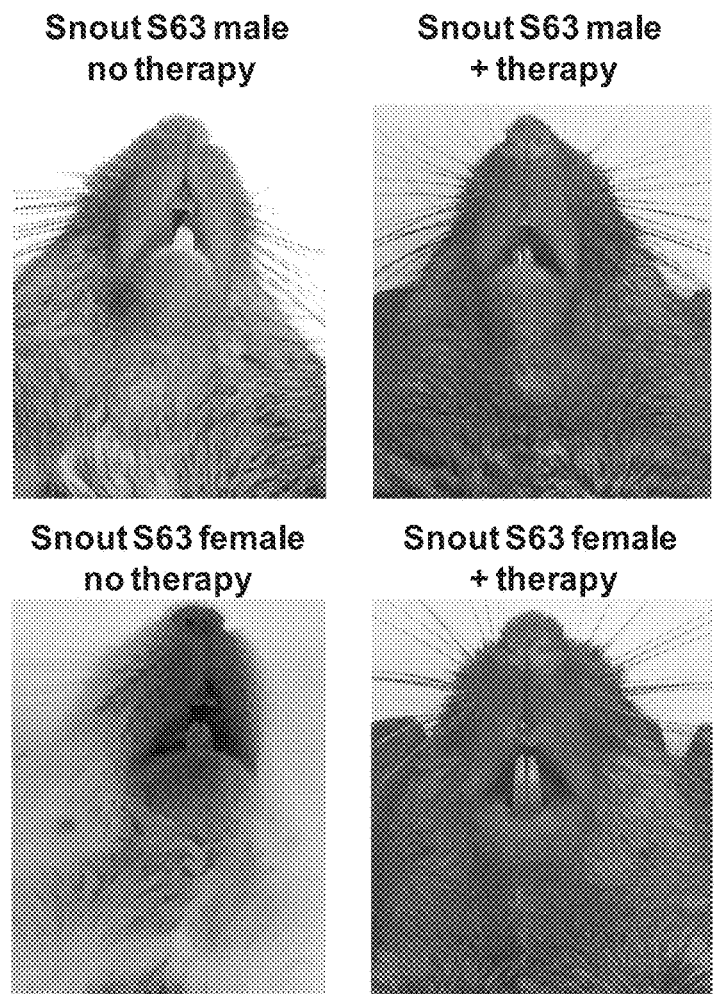

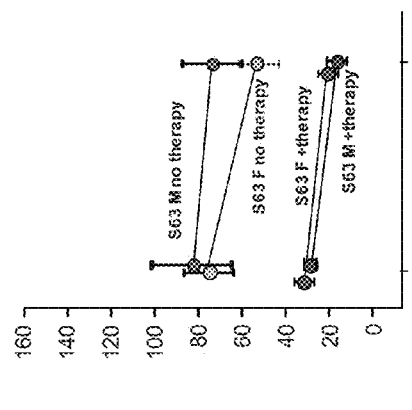
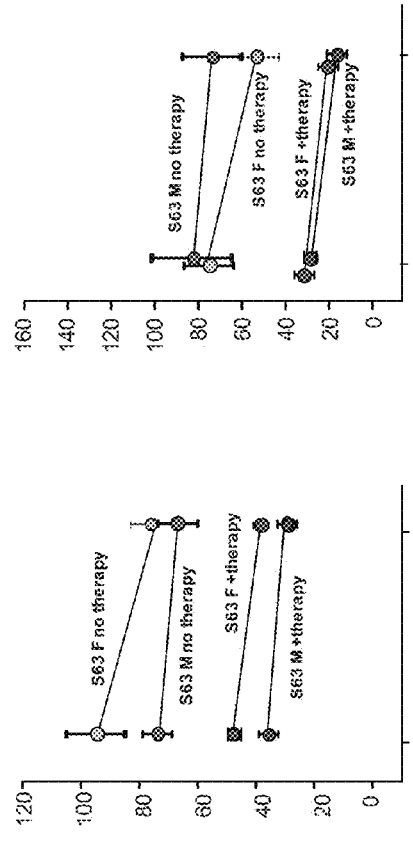
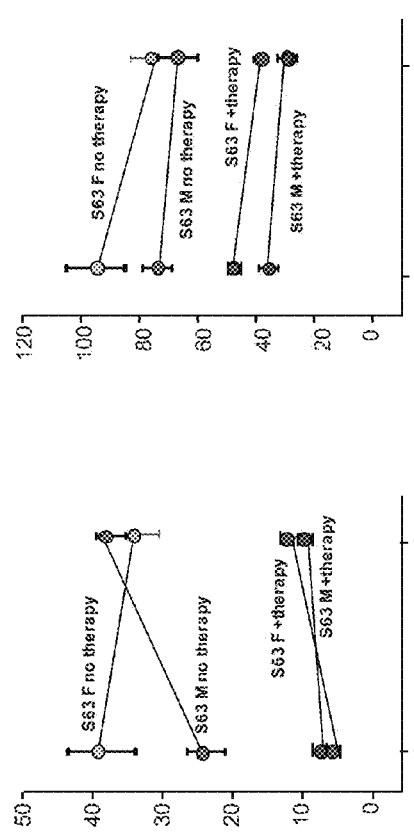
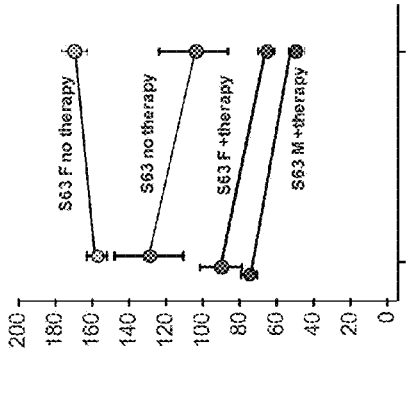
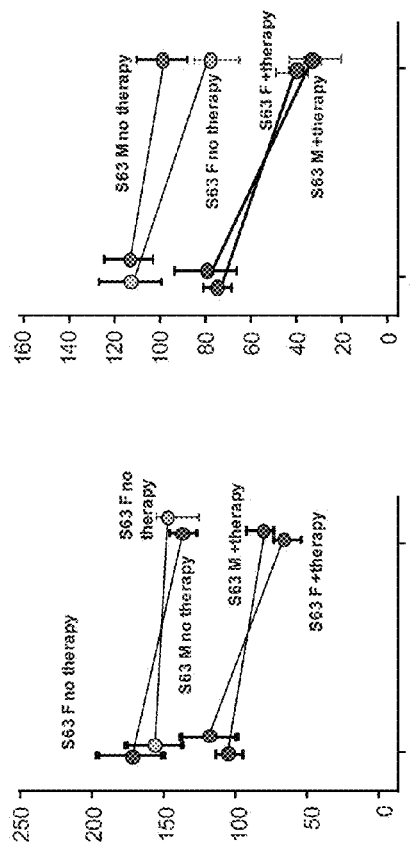

SEQUENCE LISTING

```
<160> NUMBER OF SEQ ID NOS: 8

<210> SEQ ID NO 1
<211> LENGTH: 500
<212> TYPE: PRT
<213> ORGANISM: Artificial Sequence
<220> FEATURE:
<223> OTHER INFORMATION: Synthetic AAM21515.1 (C1EI AA sequence)

<400> SEQUENCE: 1

Met Ala Ser Arg Leu Thr Leu Thr Leu Leu Leu Leu Leu Ala
1               5                   10                  15

Gly Asp Arg Ala Ser Ser Asn Pro Asn Ala Thr Ser Ser Ser Gln
                20                  25                  30

Asp Pro Glu Ser Leu Gln Asp Arg Gly Glu Gly Lys Val Ala Thr Thr
            35                  40                  45

Val Ile Ser Lys Met Leu Phe Val Glu Pro Ile Leu Glu Val Ser Ser
        50                  55                  60

Leu Pro Thr Thr Asn Ser Thr Thr Asn Ser Ala Thr Lys Ile Thr Ala
65                  70                  75                  80

Asn Thr Thr Asp Glu Pro Thr Thr Gln Pro Thr Thr Glu Pro Thr Thr
                85                  90                  95

Gln Pro Thr Ile Gln Pro Thr Gln Pro Thr Thr Gln Leu Pro Thr Asp
                100                 105                 110

Ser Pro Thr Gln Pro Thr Thr Gly Ser Phe Cys Pro Gly Pro Val Thr
                115                 120                 125

Leu Cys Ser Asp Leu Glu Ser His Ser Thr Glu Ala Val Leu Gly Asp
        130                 135                 140

Ala Leu Val Asp Phe Ser Leu Lys Leu Tyr His Ala Phe Ser Ala Met
145                 150                 155                 160

Lys Lys Val Glu Thr Asn Met Ala Phe Ser Pro Phe Ser Ile Ala Ser
                165                 170                 175

Leu Leu Thr Gln Val Leu Leu Gly Ala Gly Glu Asn Thr Lys Thr Asn
                180                 185                 190

Leu Glu Ser Ile Leu Ser Tyr Pro Lys Asp Phe Thr Cys Val His Gln
```

```
                195                 200                 205
Ala Leu Lys Gly Phe Thr Thr Lys Gly Val Thr Ser Val Ser Gln Ile
210                 215                 220

Phe His Ser Pro Asp Leu Ala Ile Arg Asp Thr Phe Val Asn Ala Ser
225                 230                 235                 240

Arg Thr Leu Tyr Ser Ser Pro Arg Val Leu Ser Asn Asn Ser Asp
                245                 250                 255

Ala Asn Leu Glu Leu Ile Asn Thr Trp Val Ala Lys Asn Thr Asn Asn
            260                 265                 270

Lys Ile Ser Arg Leu Leu Asp Ser Leu Pro Ser Asp Thr Arg Leu Val
        275                 280                 285

Leu Leu Asn Ala Ile Tyr Leu Ser Ala Lys Trp Lys Thr Thr Phe Asp
290                 295                 300

Pro Lys Lys Thr Arg Met Glu Pro Phe His Phe Lys Asn Ser Val Ile
305                 310                 315                 320

Lys Val Pro Met Met Asn Ser Lys Lys Tyr Pro Val Ala His Phe Ile
                325                 330                 335

Asp Gln Thr Leu Lys Ala Lys Val Gly Gln Leu Gln Leu Ser His Asn
            340                 345                 350

Leu Ser Leu Val Ile Leu Val Pro Gln Asn Leu Lys His Arg Leu Glu
        355                 360                 365

Asp Met Glu Gln Ala Leu Ser Pro Ser Val Phe Lys Ala Ile Met Glu
370                 375                 380

Lys Leu Glu Met Ser Lys Phe Gln Pro Thr Leu Leu Thr Leu Pro Arg
385                 390                 395                 400

Ile Lys Val Thr Thr Ser Gln Asp Met Leu Ser Ile Met Glu Lys Leu
                405                 410                 415

Glu Phe Phe Asp Phe Ser Tyr Asp Leu Asn Leu Cys Gly Leu Thr Glu
            420                 425                 430

Asp Pro Asp Leu Gln Val Ser Ala Met Gln His Gln Thr Val Leu Glu
        435                 440                 445

Leu Thr Glu Thr Gly Val Glu Ala Ala Ala Ser Ala Ile Ser Val
450                 455                 460

Ala Arg Thr Leu Leu Val Phe Glu Val Gln Gln Pro Phe Leu Phe Val
465                 470                 475                 480

Leu Trp Asp Gln Gln His Lys Phe Pro Val Phe Met Gly Arg Val Tyr
                485                 490                 495

Asp Pro Arg Ala
            500

<210> SEQ ID NO 2
<211> LENGTH: 22243
<212> TYPE: DNA
<213> ORGANISM: Artificial Sequence
<220> FEATURE:
<223> OTHER INFORMATION: Synthetic AF435921.1 (C1EI nucl. Sequence)

<400> SEQUENCE: 2
gcccagatgg cctccaggct gaccctgctg accctcctgc tgctgctgct ggctgggta       60 tgtggtccct tgtgggatgg gggacggggg tggagacggg aggcgggatg gtgcggggtg     120
cgggcggtgg ctgaggatta acccttcagg ctccggggaa tgaggagagc tcctcttggg     180
atcattgagt gtgatccttg cacacgcact cgtagatggt ggaaagagct caggactcag     240
acagatgcaa gttctaatct tggcgggcca tgtaggagct gcgcagcgtg gtcctgagga     300
```

-continued

```
cgtcactttt ctcagcctac tcctcctgat ttataaaatg ttgaataaac agatcccacc    360
ctgtccacca agcaggcttg gcaggaggat cacataggge aaggagatgg gaagcatttt    420
gtgatatcaa agcaagagtt tgttgtagaa aagagctgtg gggaggagag gtttggctgc    480
tgtgacacag acggtggtcc caggctaggg cctgtgaaga cagggaagaa tggtagcaaa    540
catacgtggg tctgggtggg ggtcaatagc agtgagaggt cccagtggtc tgggaggtca    600
tggactagaa ataaggctaa gaagtgcagg atcccaggag aaaggtaggt aggggtgtgt    660
gtatgtgcgt gtgtgtgtgt gtgcacgcgc aagttggtat cacatactca gcagatgatg    720
tagttatgag cagggagttt ggaatcagag accttgtttt gaccectage tgtttctccc    780 atttctgtga gaccctggac tagttaatat gtgtcggtat gagtttctct acctgtgaaa    840
tggagctaat gcgtggtttc tcagtggagg atctgttgac attggggctg gataattcat    900
tgctgagggg ctaccctgcg catttttagga tgttttgcag tatatctcta gcctctacgc    960
actagattcc ggtagcatct tccctgctgt ctccctgtga caaccaaaaa tgtctctgga   1020
cattgccaaa tatcccctgg gagtcaaaat tgtttcagag ccgctggcct atactacttc   1080
tctctccctc ccttcctgcc tcccttcttt cctccttccc tttcttcgtt cccttcctaa   1140
tgtgtactgt ttttccacac ccactaatgg gttgcaaccc acagtttaaa aatttactgt   1200
tctaaatcaa ggagcacaag ttcaaatgtc tgtactagcc aagcaagtga gtcaaacagg   1260
tagatattta caggaaattg caagaacata gataaatgaa acactcagc ttcactgttt    1320 ggaaaacaac ttcctacagg gcagtaattg gtcagagatt acagagtccc tgactatccc   1380
tcatcttctg cagagcacat tcctgtgcac ccccacccctc accctgtatt gccccttctc  1440
tgaggaatta gtggtggtgg ttctaagaca gattgctcat ctgccgcact gtcagaaatt   1500
actctcttgt acaggacatt ttccacatcc acaccttctc ttcctgcttt gagtatttta   1560
gaggactgtg cctcgtagta agaaaaaaat gaaactcagt ttcttgaacc acaggataga   1620
gcctcctcaa atccaaatgc taccagctcc agctcccagg atccagagag tttgcaagac   1680
agaggcgaag ggaaggtcgc aacaacagtt atctccaaga tgctattcgt tgaacccatc   1740
ctggaggttt ccagcttgcc gacaaccaac tcaacaacca attcagccac caaaataaca   1800
gctaatacca ctgatgaacc caccacacaa cccaccacag agcccaccac ccaacccacc   1860
atccaaccca cccaaccaac tacccagctc caacagatt ctcctaccca gcccactact    1920
gggtccttct gccaggacc tgttactctc tgctctgact tggagagtca ttcaacagag    1980
gccgtgttgg gggatgcttt ggtagatttc tccctgaagc tctaccacgc cttctcagca   2040
atgaagaagg tggagaccaa catggccttt tccccattca gcatcgccag cctccttacc   2100
caggtcctgc tcgtaagac cctgcttgaa ttctctccag gtcatttgtt ggacactccc   2160
ataagagtca ccaatccaga cacttacaaa gccatgcctc tgggaagaag ctgtaaaaat   2220
gggctattat atattggggg tggggtagag ggatgtatct tttcattctt gaacattcca   2280
tcatttcaca gtgatgtaat aggcacgatt gcttgtaaaa ctctgtgact atacaagaac   2340
atataaaata aggtcgcagc cactaaccat gttttcatggc aaggagaggt gataagaaag   2400
atgaaattag gcgcagtggc tcacgcctgt aatcccagca ctttgggagg ccaaggcggg   2460
tggatcacct gaggtcagga gttcaagacc agcctggcca acatggtgaa accctgtctc   2520
tactaaaaat acaaaaatta tcagggagtg gtggtgcatg cctgtaatcc cagctacttg   2580
ggcagctgag gcaggagaat cgcttgaacc caggaggtgg aggttgcagt gagccgagac   2640
cgcaccattg cactacagtc tgggtgacag agcgagactc tgtctcaaaa aaaaaaaaaa   2700
```

```
attatcagag atagacctag agtagatgtg gttagtactg ccttctagct ctgtgacctt  2760
gggcagatca ctttaacctc tctgagcctt gagtcctctt gtgtaaaata gtgatgatgc  2820
tatctacctc aaaagattaa gaagcagaaa gccaggccgg gtgcggtggt tcacacctgt  2880
aatcccagca ttttaggagg ccgaggcggg cagatcacga ggtcaggagt tcgagaccag  2940
cctgactaac atggtgaaac cccgtctcta ctaaaaataa aaagaaatta gctaggcatg  3000
gtggtgcaca cctgtaaccc cagctactca ggaggctgag gcaggagaat cacttgaaca  3060
cgggaggcag aggttgcagt gagccgaaat catgccactg cactccagcc tgggaagact  3120
gagcaagact ctgtctcaaa aaaaaaaaag aagcagccta gtgtctgact tagtgggagg  3180
tcaaaaaaat gtaaatcctc tgccatcttg agggattact gtcaagtccc atttggtaat  3240
taccctagga atggcacaaa caaattacta caagcagtgg ggacagagct attactcccc  3300
agagagaatt ctaaaaaggc tacagaatct ttcttggctg gcacggtga ctcacaccta  3360
taatcctggc actttgggag gccaaggcag gagttcaaga ccagcctggc caacatgttg  3420
aaaccccatc tctactaaaa atgcaaaaat tagccaggca tagtgatgca tgcttattgt  3480
cccagctact gggaggcag aggtggggagg attgcttgaa cctggagatt caagtgagct  3540
gagattgcac cactgcattc cagcctgggc aacaaagcaa gactctgtct caaaaaaaaa  3600
aaaaaaaaaa aaaaagaga gattgagaga acacttccag ctcagatgat ctgtgatccc  3660
ctccaaagca gggaataccc tccattccag cctggtcccc aaccctcatt cccaaggaag  3720
gcccccgact catcctgcaa gtatctttca tctctgccct tgttgcagg gctggggag  3780
aacaccaaaa caaacctgga gagcatcctc tcttacccca aggacttcac ctgtgtccac  3840
caggccctga agggcttcac gaccaaaggt gtcacctcag tctctcagat cttccacagc  3900
ccaggtgagt gcccaggaat gggcagtgtc tgcagaggag ggtcctgaga ggactctgaa  3960
gggggaccca gcgctgggga agaaaggac agagggaatg ttggagctac agtatcaggg  4020
atggactgca gagcaggtga agaccttggc aggagcatta ggtcactcca ggaactagac  4080
tgttcttcta atgagacctt agacaagtct ctggcattca tcaactgctt tagaataaaa  4140
ataaccgggc aggtacagta aaatagtgat gatgctatct acctcaaaag attaagaagc  4200
agaaagccag gctgggcgtg gtggctcaca cctgtaatcc cagcactttg ggaggccgag  4260
gcaggtggat cacgaggtca ggggttcgag accagcctga ccaacatggt gaaaccctgt  4320
ctctactaaa aatacaaaaa ttagctgggc atggtggcgg gcacctgtaa tcccagctat  4380
tcaggaggct gaggcaggag aattgcttga acctgggagg cggaggttgc agtgagccga  4440
gatgacgcca ctgcactcca gcctgggcga cagagcaaga ctccgtctca aaaaaaaaa  4500
caaaacaaa acaaaaacaa aaaaaaaac aagaaggag aaagccggc cgggcatggt  4560
ggctctcatc tgtaagttca aggagttgaa ggtatgctag gactttggga ggccaaggcc  4620
ttcaagacca gcctgggcag catggcgaaa cctgtctccca ttaaaaaaaa aaaagttggg  4680
ggtacggctg gcatggtgg ctcacacctg taatcccagc actttgggag gctgaggtgg  4740
gtggaacacc tgaggtcagg agttcaagac cagcctggcc aacatggcaa acccctgtct  4800
ctattaaaaa cacaaaaatt agcctggcat ggtggcaggc gcctataatc ccaactactc  4860
aggaggctga ggcaggagaa tcgcttgaac ccaagagagt gaaggttgca gtgagctgag  4920
atcatgccac ttcactccag cctgagtgaa acagcaaaac tctgtctcaa aaaaaaaaa  4980
aggaagaaag aaaaaaggcc aggcgcggtg actcacgcct gtaatcgcaa cactttggca  5040
```

```
ggccgaggca ggcgattcac aaggtcagga gttcgagacc agtctggcta actaacatag   5100
tgaaactccg tctctactga aaatacaaga aattaccctg gcatggtggt gtgcacctgt   5160
aatcccagct actcaggagg ctgaggcagg agaatcgctt gaacctggga ggcagaggct   5220
gcagtgagcc gagatcgcgc cactgcactc cagcctggat gacagagcaa gactctgtct   5280
caaaaaaaaa aggccgggcg cggtggctca tgcctgtaat cccagcactt tgggaggctg   5340
aggcgggcgg accacgaggt cagaagatca agaccatcct ggctaacaag atgaaaccct   5400
gtctctgcca aaaaaataca aaacttagcc gggcatggtg gcaggcgcct gtggtcccaa   5460
ctacttggga ggctgaggca ggagaatggc atgaacccgg gaggcggagc ttgcagtgag   5520
ccgagattgc gccactgcac tccagcctgg gcaacagagc gagacaccat ctcaaaaaaa   5580
aaaaaaaaaa atggggcggg cgggccaggc gcggtgtctc acacctgtaa tcccagcact   5640
ttgggaggct gaggtgggcg gatcacttga ggtcaggagt tcaagaccag cctggccaac   5700
accaggaaac cctgtctctg ttaaaaatac aaaaattagc caggtgtggt ggcacgcgcc   5760
tgtagtccca gcaggagaat aacttcaacc tgggagacag aggttgcagt cagctgagat   5820
cgcaccactg cattccagcc tgggtgacag accgagactc tgtctcaaaa aaaaaaaaaa   5880
aagaagaata cccatatgca ttcattaata tagggcta gagggctaga gagctataga   5940
cataaaatag acaaaaaatt tttttgctca ttttgggtc aaaggagtct tgggactcta   6000 attctttaa tttttgtgtt atgtgaattt gttatcattt acatgtatta tgttattaag   6060
taggtaataa tgataatact aataataaac ttacaaaacg atccaatgta gttgttttca   6120
gactttgttc ctcggagccc taggactttg caaagctgtt tctggagtca tggtgggagt   6180
ggggtgtggg gagcctgagc agtggggaag ggttcaccac ttcctgtgag agggaaacgg   6240
accagctggg ctctgagctc cccacccagc ctcagccagg gtccatttta tattgtgggc   6300
ttcagacatg cctttgtttg aaagcagttc tgctgcttta aaatgtttga taaccattga   6360
actaatctac ccacctccct ttttaaaaaa aaaggaaaa cttttttta agctgttttt   6420 tttgtttttt gtttttttt aaactgtaaa aacaatactt aggtctggct cagtgtgcct   6480
gtaattccaa cactgagagg ctgaggtagg aggattgctt gaggctagaa tttcgagact   6540
agcctctggg caacatagac agacctcatc tctacaaaaa attttaaaaa ttatccgggt   6600
gtggtacgtg tctgtagttc cagctatgaa ggactgagac gggaggattg cttgagccaa   6660
ggaattcgaa gttagagtga gctatgttta tgcctctgta ctctaggttg ggtaacagag   6720
taggaccctg tctctaaaaa aaaaaaaatt taatttaaat tttaaaaact cacctatcac   6780
cccatcatct gaaaacacc ctctttcaga tgtgggaaaa acatggctca gaggtgttca   6840
agaaatgttg catttattta ttacttacaa agctgtaagt cagctttatc cgctgtcttg   6900
ctaggttggt gaaaaatacg taacagcatt caatattagg gcttctatcc ccatctagct   6960
gcacactgga gctgtgccaa gcaaggttct tggtcttatg ttgtacttag gcatcagcaa   7020
agcctgggaa aatatctttt tttttttttt gagacagaat ctcgctctgt cgcccaggct   7080
ggaatgcagt ggcaccatct cagctcactg caacctccgt ctcccagatt caagtgattc   7140
tcctgcctca gcctcccgaa tagctgggat tacaggctgg tcttgaactc ctggcctcca   7200
gtgatccacc caccttggcc tcccaaagtg ctgcgattac aggtgtgagc caccatgccc   7260
agctggggaa aatatcttta atctacttag tcctagaaaa attatctttc aagtgctttt   7320
tttttttttt tcagtggact gaaggctttt gcagagcaaa agccaggaag ttttgtcaca   7380
aacttccacc aaggccagga agcagagtct attccgtgcc aaaattaagg gaagaaaaga   7440
```

```
gggaaaatct aggcaaatgg aatttaatat ctcaaaaaga ttatcttgcc gagccatagt   7500
cacatagcaa gctgaggcag cggaggcttg gggctacttc tcttgttctt ggttctgggt   7560
ttaccttctt tgggccttat ttgccacatc tgtaagagga gtgggctgga ccgcgctcca   7620
ccatgccgta ttcactaagt gagcagatag aaccatagaa agcatgctca ctctcaaatc   7680
gtgctcatgg aaagaacgac gtgttcagga ctcatgcctc cctttctcaa catacccca    7740 gacctggcca taagggacac cttttgtgaat gcctctcgga ccctgtacag cagcagcccc  7800
agagtcctaa gcaacaacag tgacgccaac ttggagctca tcaacacctg ggtggccaag   7860
aacaccaaca acaagatcag ccggctgcta gacagtctgc cctccgatac ccgccttgtc   7920
ctcctcaatg ctatctacct gagtggtaag ggtgccctta gccagttagt cttcccattc   7980
tgggtccttc ttcccctcct ggcttcaaag cccacttaac cccaagttct acaatcggat   8040
ctcaatgtcc ctgcactact ctttgctaac aaggctttta gctcctcttc atcctttttcc  8100 tacctgcatt agagcaaccc tcccacctct tccctctagc caagtggaag acaacatttg   8160
atcccaagaa aaccagaatg gaacccttc acttcaaaaa ctcagttata aaagtgccca    8220
tgatgaatag caagaagtac cctgtggccc atttcattga ccaaactttg aaagccaagg   8280
taagttctta acctttcctt ctcctgtttg aaacctactt gagtctcctg actttttttc   8340
tgctgtagtc ccatcatttt ggggtacatg cttacaaatt catcacttct actccttcca   8400
tctgtatttc caccctatct tttctccttc tcctttctct agccttggcc aaggcagaca   8460
ttgtatattt taggctggaa acaggattct caagtttctt catgcatctc tactatattg   8520
aatggcaaaa tgtgagtcgt gttcctattc tacacatctg tttcttttc cagtcaactc    8580 atcagaagac tctggtggct tagcaagtcc tgtgtgtatg tgggtacctg tgtacagcat   8640
acatatacat gtgtagacgt gtataagtat atccttgtat atgcatatat gtggtaagtg   8700
catgtgtgca catgagttaa atggcttaag tgcattagca gaaattgaac aatttagttt   8760
gatgagtagg gagggagaga agacagaata tggagcccag aggatcccaa ctggcaagct   8820
atctcatccc cagttaccag atatttccac ctttttagga tggcaaaaca cagacctatg   8880
agacagaaaa cagtaagaga caatgtctca atacctggct gagaaacaaa ggctctgttc   8940
ttggaacatg ctaggcttgg ttccacattg ggagctttcc ttagcttttg tttctgcctg   9000
tatccctctt cactcagatc ctcacatagc ttgttccttc ttgtcatttg ggtgtcagct   9060
cagaggtcac cttggtggag aagtcttctc cccattaaag cagcctcctc ctcaccctgt   9120
aatatcactc ctgttttatt atattcatta cactcatcac catctgaaat tatgtcattt   9180
atttgcttat ttgcctagga cattgtctgt ctccctaaga tactgtctct ctacttgaat   9240
acaggaacct gtcttgtttc cttctgtatc tgtagtgcct agaacaatgc ctcctatcat   9300
aggtgctcat tcagtgtttg ctgaataaat gaatgaatga aatagagggt gccaaagaga   9360
gctactcagt aaaagtggct ggaagacttc atagaggagg gttttttttc gagacagggt   9420
ctcactctgt cactcaagct gcagtgcatt gacatgatct cagctcactg caatctctgc   9480
ctcccgagtt caagcagttc tcctgcctca gcctcccaag tagctgggac tacaggagcc   9540
cgccaccaca cctggctaat ttttgtattt ttagtagaga cggggtttca ccatgttagc   9600
caagctggtc tcgaactcct gacctcaagt gatccacacc ctcagcctcc caagggctg    9660 ggattacagg catgagccac agcacccagc tgaggaggtt atttttgacc attctttgct   9720
cagttattta tccactcatg gacttatcca cccatctatc catccctatc taatgtattt   9780
```

```
gaccattcat gactcattta gcagaaccag gacagcctgt ataaggcaca gaagagtgaa    9840
tatatgtgac aggtccagag cattgttcaa attcaagata cgttggggga ggtataaata    9900
tgagattttt ttcaaatcaa ttggaatggc tatttaatca aagccataga tgttaggtgg    9960
aaagtaggaa ttaagaactt aacaagttag gtttaaatgt aactattcga attataagaa   10020
caagtatttc ctctctaaaa atgttttttaa agtttcacac aaaactctaa accaaaaatc   10080
attgtaaaaa tcccttggga gtagactgtt gaaaccattg aggtgaggtg ataggttaag   10140
gtgagcattc tggacatata atatcaataa taaatattca aatacaaagc aggtataata   10200
tgaagagtaa tttctatctc cccaagccaa tatgagtttt gtttgtttgt ttgttttct    10260 tttgagataa agtctcattc tgttgcccag gccggagtgc agtggcacaa tcccagctct   10320
ctgtaacctc tgcctcccag gttcaagcga ttctcctgcc ttagcctccc tagtagctgg   10380
gattataggc gcctgccacc actcccagct aattttttgta tttttagtag agatgggggtt 10440 tcaccatgtt ggccaggctg gtcatgaact cctgacctca gtgctcgtc cgtcttcggc    10500 ctcctaaagt gctggcatta caggcgtgag ccactgcacc cagcctgagt ttttttttt    10560 tttttaagcc aaaggaggag gagtagtttt gtgcacaaaa gccactattt agagttcctt   10620
aggttttaaa cagataatta attttaatgta ctaacaaatg caaaattaaa attttactta 10680
tgccttttaa ttttaagctg aacttgctac attaagagta gggtgatttg gctgggcgca   10740
gtggctcatg cctataatcc cagcacttta ggaggctgag gcaggtggat cacttgaagc   10800
taagagtttg agaccagcct ggccaacatg gtggaattct gtctctacta aaaatacaaa   10860
aattagccag gcatggtggc acatgtctgt aatcccagct actcaggatg ctaaggcaca   10920
gaatcacttg aacctgggag gcagaggtta cagtgagcca aaatcgcgcc actgcactcc   10980
aacctgggca acacagcaag actctgtctc aaaacacaaa aaaagaatag gctgggtaca   11040
gtggctcacg cctgtaatcc cagcactttg ggaggccgag gcaggtgaat cacctgaggt   11100
caggagttcg agaccagctt ggccaacatt gtgaaacccc atctccatta aaaatacaaa   11160
aaataagccg ggtgtgatgg tgcacgcctg taatcccaga tacttgggag gctgggacag   11220
aagaatcgct tgaacccggg aggcgaaggt tgcagtgagc cgagatcatg ccactgcatt   11280
ccagcctgag cgacagagtg agaccttgtc tcagaaaaaa aaaataggg tgatttttat    11340 ataaaaacac tctcatttgt tcttgaatta attgccatat tgaacagatt aaactccttt   11400
aaaccatttt ttctatctac aaacataatt agtattccca taagcatttt aagctccctt   11460
taaaaattta atatgctcga ttttcttttt tctttttattt atttatgtag ttttcccaga   11520
cagggtctta ctctatcacc cagtctggag tacagtgaca caatcctcac ttactgtaac   11580
ctcaagctcc ttgggatgaa gcagtcctcc caccctagcc tcttaagtag ctgagattcc   11640
aggcatgagc cacctcaccc agctgatttt cttttttaaac acatctaata cctgacaggt   11700
cgtaattacg actgtgcttg gccatatcat cctaacaccct aaagctcact tgtaaactga   11760
aaattaaatt tgaagggtga attaacttct agccaacatt ccaatatcat tctcacattt   11820
aatgaaatta tcctacaact ttgcttaaaa gcataaaact agcatgtcag agtctcttaa   11880
aaattacaat cactattta aataacaaac atacaggtta ccctgaactt aacacctggt   11940
tttaacatga tgaagttggt ttcttttgtc attcttatac taaattctaa atcttcctgg   12000
cacttaagga tatttaccca aggaaggggg tgagatttac cggctcaggt acaccgaggt   12060
tactggcttg aaaattcaag accacagcat ggtaaatttt tcttcagaga ttcaaggttc   12120
atacatagga cttgaagggc acatgctact caaatgagta tatccaactt gagtgctaca   12180
```

```
tcaacaggga ccccatgtcc actcttttca gtcgaaattg gcttactatc tacttcttct   12240
gggctattca gtttccgaca attgattgct ttcagttaat ttctttattg cccagttgaa   12300
ttctgcattc ttctagattc ttttttgttcc ttcagcctca atcataatac catttaatga   12360
cagtctcata tcctattaga ctagggtttc tcagccttgg cactattgac atattgggtc   12420
agataattct ttgtcctgtg cattgtagaa tttagcatct tccttagctt ctactcacta   12480
gaagccagta gcactgtgtg cacatcctcc ttgcccctg ccagctatga caaccaaaat   12540
gtctccagac attaccaaat gtccactgag aggcaaattc actctgagtt gacaacccct   12600
gtattaaacc caggggccct gcacttctta catacttttg tctggtcacc agttgaaagt   12660
ccttcttctt ttttttttct cttttgaga tggagtctcg ctctgtcacc aggctggagt   12720
gcagtggcat gatctcggct cactgcagcc tccacctccc gggttcaagc aattctcctg   12780
cctcagcctc ctgagtagct gggattacag gcacgtgcca cccagct aattttttgta   12840 tttttagtag aggtgggtt tcatcatggt ggccaggatg gtctcaatct cttgacctca   12900
tgatccgccc acctcggcct cccaaagtgc tgggattaca ggtgtgagcc accgtgcatg   12960
accaaaagtc cttctaatag caaagtggaa aggtaggctg tgaacaatct tgaatgccat   13020
actaagattt gtacttattc tcataggcag tgaagagcca tcaatagttt ttacagaggc   13080
tgacctgata actctggcgg ttcaatgtgc atgctatata ctatatgcac aacacattag   13140
gaaggaaggg aacagcgctc agagaaatca aatcacttgc ccatattaca tagctcgtca   13200
gtggtggagt cagggtataa tcagaaactc atgctccttc ctctacctct ccccagcaca   13260
gagttggatc agcactgttc acccagctgg tatccccatt tcatggtaaa gcctggaagc   13320
ttaggtctga ctgatgcttg ttgaaataca gactgtggga gcagactgca ggacagcatt   13380
gtgacagagg gtggggccag gagagagatg cggtaggaag actgttaagg tgcatctctt   13440
attttctagg tgggggcagct gcagctctcc cacaatctga gtttggtgat cctggtaccc   13500
cagaacctga aacatcgtct tgaagacatg gaacaggctc tcagcccttc tgttttcaag   13560
gccatcatgg agaaactgga gatgtccaag ttccagccca ctctcctaac actaccccgc   13620
atcaaagtga cgaccagcca ggatatgctc tcaatcatgg agaaattggg tgagctctgg   13680
cagcttaggg ttactcccag gccatcagag gagaaagggg ggatccctaa gatgtagtta   13740
gcattctcta gagtattttt tacatccata atctcagttt gtcctgcaac cctgcaagtt   13800
agaggggtag gtgctattat cccattggat cattgtggaa atggaggctc agaagcttta   13860
tgtgacttac ccagagattc catgatttac ccttgagcta gtcagaggca aaccagaaca   13920
ccgacccagg tctccagctc tcctgagttt tttctatggt tccttgtgac ataggcagtg   13980
gaacagtggg acaggtaacc gaggtgaatt atggatgctc cttccccaga cacatttcaa   14040
aacagtcagc caccccgtgg aatatgcaag aagctatctg gaagtgcaga tctggaggct   14100
tctgagttta cgagaggcaa cagagactcc attttctttt tttttttttt tttgagacg   14160 gagtcttgct ctgtcaccca ggacaggctg gagtgcagtg gtgcgatctc tgctcactgc   14220
aagatccgcc tcccagattc acgccatgcc attctctcgc ctcagcctcc cgagtagctg   14280
ggactacagg tgcccgccac cacgcctggc taatttttgtt tttgtatttt tagtagagac   14340
ggggtttcac tgtgttaacc aggatggtca caatctccgg accttgtgat ccacctgcct   14400
cggcctccca aagtgctggg attacaggca tgagtcaccg cgcccagccc agagactcca   14460
ttttctaacc tttgtttttt tgtttgtttg ttttttgagac ggagcctcac tctgtcaccc   14520
```

```
aggctggagc gcagtggcat gatcttgggt cactgcaacc tccgcctcct gggttcaagt    14580
gattctccta cctcagcctc ccaagtagct gggattacag gcacctacca ccacgcccag    14640 ctaattttt tgtattttta gtagagatgg ggtttcacca tgttggtgaa gctggtcttg     14700
aactcctggg ctcaagtgat ccacccacct cggcttccca aagtgctggg attacaggtg    14760
tgagccactg tgcccagcct cattttctaa cctttgatct catgtccagc cctgtcactt    14820
catttcttgt tagagaattt gaccgcctaa cacatgattc catttccttg tatatgtcat    14880
ctgtatagga agaaaacctc ttttttattt tcattcaaca cttctggcca ccaaacaggt    14940
gtgggagtgt tttctaagca attctccagt tatctgggga caccaactgg gtgtcctaca    15000
attgaatcca attctaacac tctacctgga ataacatca gatcccgtgc agtttaagtg      15060
ctccgcccca gcaaatttcc ccccgttttcc aatgtcagtt acaagactgg gttgtcacct   15120
gtgcatcaga ccaaccagct ataatttgga gattcccaca actccctgct agggtttcat    15180
catttgctag aatagctgac aaaactcagg agacacttac atttactggt ttattatgta    15240
aaggattaag taaaggatac agatgaacag ccagttgaag agatacatag ggcaaaatct    15300
ggaagggtcc tgggcccagc agcatctatc ctgtggagtt ctgtttgcta ccttcctgac    15360
acatgtatgt gttcaccaac cagaaactct cagaaccctg tacttaggga gaagtcatca    15420
tgtaggcatg attgattatt acccaatctc cagctcctct cttctcccca gaggatggag    15480
agaggggctg aaagttccaa gcttctaatc acacttggtc tttctggtga ccagccccaa    15540
tccaggagcc agcaggagta gcctcattag cacaaaaggc attcctatga cccaggaaat    15600
tccaagggat ctagtagctc tgtgtcagga actgggatcg gagaccaaat attagatggt    15660
ctaatatttg gagctaaaga tgctcctata gcatattttc ccattatttc acagcatcat    15720
ggcattgcat ataacctcat ttttcatat atgacctatc tctgatctat tacctcacct     15780
ccaaggtcct gggagataag gaggcaatga catcattttt cagggttgtt ttagggatga    15840
ggggcaaggc ctctcacctt gagagagagt ggcagtgttg gcccactaa tagaggatcc      15900 cacgaactgc cagagggtac agtatgtaat ctggcaaaca agggaagagg aagagagcac    15960
tgggactcag gatgaaccca gagaattcag gacaaaggtc tccatcagct gagggtatca    16020
tgctggcttc tgactctgtt tttctctggt tttgccctag aattcttcga ttttcttat     16080 gaccttaacc tgtgtgggct gacagaggac ccagatcttc aggtttctgc gatgcagcac    16140
cagacagtgc tggaactgac agagactggg gtggaggcgg ctgcagcctc cgccatctct    16200
gtggcccgca ccctgctggt cttttgaagtg cagcagccct tcctcttcgt gctctgggac   16260
cagcagcaca agttccctgt cttcatgggg cgagtatatg accccagggc ctgagacctg    16320
caggatcagg ttagggcgag cgctaccctct ccagcctcag ctctcagttg cagccctgct   16380
gctgcctgcc tggacttggc ccctgccacc tcctgcctca ggtgtccgct atccaccaaa    16440
agggctccct gagggtctgg gcaagggacc tgcttctatt agcccttctc catggccctg    16500
ccatgctctc caaccacttt tttgcagctt tctctagttc aagttcacca gactctataa    16560
ataaaacctg acagaccatg actttctctg ctttgccttt gttttttat ttttattt       16620 ttatttttt taggcagggt ctcaatctgt caccaggct agagtacagt ggtgagatca      16680
tggttcactg cagccttaac ctcctgagct caaacaatcc tcccatctca gcctcctatg    16740
taggtgggac cacatgggct tgccaccatg cccagctaat ttttaaattt tttgtaaaga    16800
cagggtctta ctatgttgcc taggctggtc tccaactcct gggctcaagc aatcatccta   16860
acacagcctc ccgaagtgct gggattgtag gcacaccata cctctccttt gcctttgaat    16920
```

```
atcagctgct tcaatactaa aggacaagag cgcccatggt tcctgtatca gccagctatt    16980
gctgtatagt aagtcacgtt aaacttagtg gcttcaaaca gcaacccttt gttattttat    17040
gtaagtttca gagttgacta ggtgttttgc tgatctgggc tgaacctggc tgatcttccc    17100
tgggctcatt catacatctg taaggtatag ttgttgggtt ggttaggggga tgactggtct    17160 tctgtggcct cagccatgac accaggacaa cttggctctt ctacatgtct tgtatgtcct    17220
tccaacaggc tagtctgtaa tggaaaagag tcaaacagcc agtctctttt tgtttaccat    17280
tgtcctgcag ccaaagcaaa tcacaggacc aaacctagag ttagactgga aaagcactac    17340
aaagtgacag ggcaaagaga cgttaattgg ggactattca tgcagtccat ttctcacagc    17400
ccctatcttg cttatttgtc tgcaacaact ctgacaacaa taatgacagt agctaacgtt    17460
gggaacatag gcagtctgct aagagttttg caggcattta atcttcacaa taatttata    17520 tggtaaattc agagaggcta agtcttgttc aaagtcctgt agttaggaaa tgatgaaact    17580
gagatttaat agcacctctt atgactcttt ttttttgag acaaagtttc tcttttgttg    17640
ccaaggcttg agtataatag cacaatctcg gctcactgta acctctgcct cctgggttca    17700
agtgattctc ctgcctcagc ctcccaagta gctgggatta caagcatgca ctaccacacc    17760
tggctaattt tgtatttta gtagagacag gttttctttt ttttttttt tccgagatgg    17820 agtcttgctt tgtcggccag gctggagtgc agtggtgcaa tcttggctta ctcaacctcc    17880
acctcccggg ttcaagtagt tctgcctcag cctcccaagt agctgggatt acaggcgtgc    17940
accaccaagc ccagctaact tttgtatttt tagtagagac ggggtttcac catgtggacc    18000
aggctggtct caaactcctg actccaagtg atcttcccac ctcagcctcc caaagtgctg    18060
gcattacagg tgtgagccac tgtgcccggc ctagtgaaaa caatcttctt tactcagtct    18120
accagctcaa ataccagtct cttcaggaaa caacctcaca gacacaccca gaaatgatat    18180
cttaccagtt gtctgggcat ccctttagccc agtaaaattg acacataaat ttaaccaccc    18240
cacaccttcc cttctcagtt tcccaaagtc aatctctcag gctgctggga agaccccaaa    18300
ttcctgtctg ggtgggtccc gctttgattc ttatgtgagg aactgttgaa agcaaaggca    18360
ccccccaaat tcaggaagat tcccctctcc ttggggagat cctgacatga tgaaggtggt    18420
gctcagcacc aacctgaatt gtgaaccaac aaagtcagga ggtggaaggt gattctgacc    18480
cctgtggggg tcaaatctct ttgacccttc caatcatgct gagcccggta atgttcccgt    18540
ttgtgaaatg atgaagccaa aactcagaga ggttaagtaa ctatccaaag gtcagactgc    18600
tgcaaatcga tcccacatta tccaaattca agtgtagtag ataacttatt tgggcaggct    18660
tatttccttt ctgcccaaac ttgactgtaa cttaaatctg tgtcttctta ctccctgcac    18720
catgtgaccc tacagagctt atcaaagtgt cttgcactta aaaaaaaaaa aactatggag    18780
gctgggcata gtggctcatg cctataatgc cagcactttg ggagacggag gcaggcagat    18840
cacttgaggc cagggttttg agaccagcct gggcaacatg gcgaaacct gtctctatta    18900 aaaaatacaa aaatgagcca ggtgttgtgg tgcatgcctg taatcccagc tactcgggag    18960
gctgaggcat gagaatcact ttaacctgga aggcagaggt tgcagtgaat ccagattgta    19020
ccactccact ccagcctggg tgacagagtg agagactgtc taaaaaaaaa aactatgaaa    19080
tgaatgatta aatgaatgag ttatcacatc caggtagagg gaaagaggag atacctaccc    19140
atctggaaag catagaaaaa tctggaaatg aagagaattt attattat tttattttt    19200 gagacagagt cttgctctat cacccaggct ggagtgcagc ggcttgaaca tggttcactg    19260
```

```
cagccttgac ctcctgggct caggtgatcc ttccacttca gcctcctgag tagcagggac   19320
cacaggtgtg caccaccaca cctggctaca ttttttgttt tttataaaga cagggtctca   19380
gctgggcacg gtggctcatg cctgtaatgc cagcactttg ggaggccaag gcaggctgat   19440
cacctgagct caggagttcg agaccagcct ggcccacatg gtgaaacctc gtctctatta   19500
aaaatacaaa aattaacaag gcgtggcagc aggcacatgt aatcccagct acttgcgggc   19560
tgaggcagga gaatcacttg aacccaagag gtggaggttg cagtgagccg agatcatgcc   19620
actgcactcc tccagtctgg gggatggagc aagacttcgc cttggagaaa aaaaaaaaaa   19680
gtctcactgt gttgcccaag ctggtctgga actcctgggc tcaagagatc ctctagcctt   19740
ggcctcccaa aatgttggga ttactggtgt gagccaccac acccaagata atttaaatat   19800
tttctcttct gaagcttttc ttataagagg gcatgtgtca cttttttcgt tgtttaaaa    19860
caatgaacat ttattttgct ttgttttggt ttttgtttt tgttttgtt ttgagacgga     19920
gtcttgctct gtcttgccca ggctggagta cagtgacaca atctcggctc actgcagcct   19980
ccgcctcctg ggttcaaaca attctcctgt ctcagcctcc cgagtagctg ggactacagg   20040
cttgtgccac catgcctagc taattttttgt atctttagta gaaacgaggt ttcactatgt   20100
tggccaggct ggtctcgaac tcctgacctc aggtgacctg ccctccttgg cccccccaaag  20160
tgccgggatt acaggtataa gccactgcac ccagcctgaa catttatttt gctaatgagt   20220
cattgaccca gtgtgggctt ggcaaatcta gggtagcctc agttatgtac ctgctacagt   20280
cagctggggg ttagctgaag gtttgttgag gtttgatttc actgagcttg cataggctct   20340
ttcacatgtt ttagactttg gctgggatca accagatgac caattctgat ccaagtgatc   20400
tctggtcttc caggaagcta gtctggctta ttcatacgaa gtttgcaaaa gtccaagaaa   20460
gcaagcagag gcatgcatgc aaggcctctt gaatccgaag ctaggaacta ctagaacatc   20520
acttctgcct cattctagca gccaaagcaa gtcaccagac cagtttagat tcaaggtaag   20580
gaaagaatct ctacctgtta aagaaaagac ctgcaaagtc attctgctaa gggcattaat   20640
ataacgaaat gtgaataatt ctggccactt ttccagtata ccatatgtgg tcttacatag   20700
ttgcaaacaa ctattagcaa ctttccccag caacctgcca ctctgttttt ccctaaagaa   20760
tcaagggctt ttgtcgagat cataataata ttagaaacac tttgttacat gaagtttcaa   20820
gtcgtttgca tataaattga atcttctgtt gctatctctg tggcatattt aacaatctct   20880
ggctcttcca gctgcctgtg ttgtagaata aattattata aatacagagc tgcctgagta   20940
tttataataa taaataaata aattatcttc atttccattt cccttgagaa agatggacag   21000
agggctatgc actcatagac acacacacac acacacacac acacccctt acaaccccca    21060
cctttctgcc ctgccttgca attctactct ggggtagaca aaggcctgta tgtccacaga   21120
tccatttca gtgatctgtt tcctgtcccc aactgtagac ccctccacac gtggatttgt    21180
ctggggaaga accttaaggt gagattaggg ttccattgca atgagtcttt gctgccactt   21240
ggtgtcattg ttgaaggctt gtcctgcata gccccatgga cacttgcctt ttcagggaga   21300
tgttttttgct gttccagatt ctttttttttt tttttttttg agacagaatc tctctctgtt  21360
gcccagactg gagtgcaatg gtgcgatctt ggctcactgc aacctctgtt tcccaggttg   21420
aagggattct cctgcctcag cttcctgagt agcaggaatt ataggcaccc accatgtgtc   21480
cagctaattt ttgtattttt agtagagatg gggttttacc atgttggcca ggctggtctc   21540
aaactcctga cctcaagtga tccacccatc ttggcctccc aaagtgttag aattacaggt   21600
gtgagtcact gtgcctggcc ggttccagat tcttaaacag ctgatgtggg gacttaaact   21660
```

```
ttgattccaa agtttacact ttacacttgt tcagccactg tttctcaaag atcaataccc     21720
ttagttctct ctggatagca gaaggcttcc aacatgagcc ataggctatg tcagaatcag     21780
cctcatccct atgaaccctt aggacattgt cttgactcat ggttgataac cacattagcc     21840
atgtatctac ctaacatgca ttaaccattt gccatgctgt caggcactgt gttaagaatt     21900
ttacatggat tatgttattt catttaagag agatcatgac ttaagaaaag gatatgttac     21960
tgaatatatt agataattca aaatttagat aatttgatac taagttttcc agaataataa     22020
ctgtaaaagg tagggagaga atcttcaacc attgtagaat tcttgtctt caaactattg      22080 tttattttct aaatacaaaa atctctaata tttctcagag taggcactct taaattaact     22140
gcttggcata tcaggacagc tatttgggct ttttcatagt gtcttatcat atctaacttt     22200
cattacaaag ttattgattt tggagggtgt ttttagcact agt                       22243

<210> SEQ ID NO 3
<211> LENGTH: 615
<212> TYPE: PRT
<213> ORGANISM: Artificial Sequence
<220> FEATURE:
<223> OTHER INFORMATION: Synthetic AAB59490.1 (FactorXII - AA)

<400> SEQUENCE: 3

Met Arg Ala Leu Leu Leu Gly Phe Leu Leu Val Ser Leu Glu Ser
1               5                   10                  15

Thr Leu Ser Ile Pro Pro Trp Glu Ala Pro Lys Glu His Lys Tyr Lys
            20                  25                  30

Ala Glu Glu His Thr Val Val Leu Thr Val Thr Gly Glu Pro Cys His
            35                  40                  45

Phe Pro Phe Gln Tyr His Arg Gln Leu Tyr His Lys Cys Thr His Lys
        50                  55                  60

Gly Arg Pro Gly Pro Gln Pro Trp Cys Ala Thr Thr Pro Asn Phe Asp
65                  70                  75                  80

Gln Asp Gln Arg Trp Gly Tyr Cys Leu Glu Pro Lys Lys Val Lys Asp
                85                  90                  95

His Cys Ser Lys His Ser Pro Cys Gln Lys Gly Gly Thr Cys Val Asn
            100                 105                 110

Met Pro Ser Gly Pro His Cys Leu Cys Pro Gln His Leu Thr Gly Asn
        115                 120                 125

His Cys Gln Lys Glu Lys Cys Phe Glu Pro Gln Leu Leu Arg Phe Phe
    130                 135                 140

His Lys Asn Glu Ile Trp Tyr Arg Thr Glu Gln Ala Ala Val Ala Arg
145                 150                 155                 160

Cys Gln Cys Lys Gly Pro Asp Ala His Cys Gln Arg Leu Ala Ser Gln
                165                 170                 175

Ala Cys Arg Thr Asn Pro Cys Leu His Gly Gly Arg Cys Leu Glu Val
            180                 185                 190

Glu Gly His Arg Leu Cys His Cys Pro Val Gly Tyr Thr Gly Pro Phe
        195                 200                 205

Cys Asp Val Asp Thr Lys Ala Ser Cys Tyr Asp Gly Arg Gly Leu Ser
    210                 215                 220

Tyr Arg Gly Leu Ala Arg Thr Thr Leu Ser Gly Ala Pro Cys Gln Pro
225                 230                 235                 240

Trp Ala Ser Glu Ala Thr Tyr Arg Asn Val Thr Ala Glu Gln Ala Arg
                245                 250                 255
```

```
Asn Trp Gly Leu Gly Gly His Ala Phe Cys Arg Asn Pro Asp Asn Asp
            260                 265                 270

Ile Arg Pro Trp Cys Phe Val Leu Asn Arg Asp Arg Leu Ser Trp Glu
        275                 280                 285

Tyr Cys Asp Leu Ala Gln Cys Gln Thr Pro Thr Gln Ala Ala Pro Pro
    290                 295                 300

Thr Pro Val Ser Pro Arg Leu His Val Pro Leu Met Pro Ala Gln Pro
305                 310                 315                 320

Ala Pro Pro Lys Pro Gln Pro Thr Thr Arg Thr Pro Pro Gln Ser Gln
                325                 330                 335

Thr Pro Gly Ala Leu Pro Ala Lys Arg Glu Gln Pro Pro Ser Leu Thr
            340                 345                 350

Arg Asn Gly Pro Leu Ser Cys Gly Gln Arg Leu Arg Lys Ser Leu Ser
        355                 360                 365

Ser Met Thr Arg Val Val Gly Gly Leu Val Ala Leu Arg Gly Ala His
    370                 375                 380

Pro Tyr Ile Ala Ala Leu Tyr Trp Gly His Ser Phe Cys Ala Gly Ser
385                 390                 395                 400

Leu Ile Ala Pro Cys Trp Val Leu Thr Ala Ala His Cys Leu Gln Asp
                405                 410                 415

Arg Pro Ala Pro Glu Asp Leu Thr Val Val Leu Gly Gln Glu Arg Arg
            420                 425                 430

Asn His Ser Cys Glu Pro Cys Gln Thr Leu Ala Val Arg Ser Tyr Arg
        435                 440                 445

Leu His Glu Ala Phe Ser Pro Val Ser Tyr Gln His Asp Leu Ala Leu
    450                 455                 460

Leu Arg Leu Gln Glu Asp Ala Asp Gly Ser Cys Ala Leu Leu Ser Pro
465                 470                 475                 480

Tyr Val Gln Pro Val Cys Leu Pro Ser Gly Ala Ala Arg Pro Ser Glu
                485                 490                 495

Thr Thr Leu Cys Gln Val Ala Gly Trp Gly His Gln Phe Glu Gly Ala
            500                 505                 510

Glu Glu Tyr Ala Ser Phe Leu Gln Glu Ala Gln Val Pro Phe Leu Ser
        515                 520                 525

Leu Glu Arg Cys Ser Ala Pro Asp Val His Gly Ser Ser Ile Leu Pro
    530                 535                 540

Gly Met Leu Cys Ala Gly Phe Leu Glu Gly Gly Thr Asp Ala Cys Gln
545                 550                 555                 560

Gly Asp Ser Gly Gly Pro Leu Val Cys Glu Asp Gln Ala Ala Glu Arg
                565                 570                 575

Arg Leu Thr Leu Gln Gly Ile Ile Ser Trp Gly Ser Gly Cys Gly Asp
            580                 585                 590

Arg Asn Lys Pro Gly Val Tyr Thr Asp Val Ala Tyr Tyr Leu Ala Trp
        595                 600                 605

Ile Arg Glu His Thr Val Ser
    610                 615

<210> SEQ ID NO 4
<211> LENGTH: 1959
<212> TYPE: DNA
<213> ORGANISM: Artificial Sequence
<220> FEATURE:
<223> OTHER INFORMATION: Synthetic M11723.1 (FactorXII - Nucleotide)

<400> SEQUENCE: 4
```

```
ttggagtcaa cactttcgat tccaccttgg aagcccccca aggagcataa gtacaaagct    60
gaagagcaca cagtcgttct cactgtcacc ggggagccct gccacttccc cttccagtac   120
caccggcagc tgtaccacaa atgtacccac aagggccggc caggccctca gccctggtgt   180
gctaccaccc ccaactttga tcaggaccag cgatggggat actgtttgga gcccaagaaa   240
gtgaaagacc actgcagcaa acacagcccc tgccagaaag agggacctg tgtgaacatg    300 ccaagcggcc cccactgtct ctgtccacaa cacctcactg gaaaccactg ccagaaagag   360
aagtgctttg agcctcagct tctccggttt ttccacaaga atgagatatg gtatagaact   420
gagcaagcag ctgtggccag atgccagtgc aagggtcctg atgccactg ccagcggctg    480 gccagccagg cctgccgcac caacccgtgc ctccatgggg gtcgctgcct agaggtggag   540
ggccaccgcc tgtgccactg cccggtgggc tacaccggac ccttctgcga cgtggacacc   600
aaggcaagct gctatgatgg ccgcgggctc agctaccgcg gcctggccag gaccacgctc   660
tcgggtgcgc cctgtcagcc gtgggcctcg gaggccacct accggaacgt gactgccgag   720
caagcgcgga actggggact gggcggccac gccttctgcc ggaaccccga caacgacatc   780
cgcccgtggt gcttcgtgct gaaccgcgac cggctgagct gggagtactg cgacctggca   840
cagtgccaga ccccaaccca ggcggcgcct ccgaccccgg tgtcccctag gcttcatgtc   900
ccactcatgc ccgcgcagcc ggcaccgccg aagcctcagc ccacgacccg gaccccgtct   960
cagtcccaga ccccggggagc cttgcgcgcg aagcgggagc agccgccttc cctgaccagg  1020
aacggcccac tgagctgcgg gcagcggctc cgcaagagtc tgtcttcgat gacccgcgtc  1080
gttggcgggc tggtggcgct acgcggggcg caccgctaca tcgccgcgct gtactggggc  1140
cacagtttct gcgccggcag cctcatcgcc cctgctggg tgctgacggc cgctcactgc  1200
ctgcaggacc ggcccgcacc cgaggatctg acggtggtgc tcggccagga acgccgtaac  1260
cacagctgtg agccgtgcca gacgttggcc gtgcgctcct accgcttgca cgaggccttc  1320
tcgcccgtca gctaccagca cgacctggct ctgttgcgcc ttcaggagga tgcggacggc  1380
agctgcgcgc tcctgtcgcc ttacgttcag ccggtgtgcc tgccaagcgg cgccgcgcga  1440
ccctccgaga ccacgctctg ccaggtggcc ggctggggcc accagttcga ggggcggag   1500 gaatatgcca gcttcctgca ggaggcgcag gtaccgttcc tctccctgga gcgctgctca  1560
gccccggacg tgcacggatc ctccatcctc cccggcatgc tctgcgcagg gttcctcgag  1620
ggcggcaccg atgcgtgcca gggtgattcc ggaggcccgc tggtgtgtga ggaccaagct  1680
gcagagcgcc ggctcaccct gcaaggcatc atcagctggg gatcgggctg tggtgaccgc  1740
aacaagccag gcgtctacac cgatgtggcc tactacctgg cctggatccg ggagcacacc  1800
gtttcctgat tgctcaggga ctcatctttc cctccttggt gattccgcag tgagagagtg  1860
gctggggcat ggaaggcaag attgtgtccc attccccag tgcggccagc tccgcgccag   1920
gatggcgcag gaactcaata aagtgctttg aaaatgctg                         1959
```

<210> SEQ ID NO 5  
<211> LENGTH: 62  
<212> TYPE: DNA  
<213> ORGANISM: Artificial Sequence  
<220> FEATURE:  
<223> OTHER INFORMATION: Synthetic

<400> SEQUENCE: 5

```
aaaagcagag agagcttccc tgaaagagat gactcctgga gtcccccaga gcctacagta    60
ct                                                                   62
```

```
<210> SEQ ID NO 6
<211> LENGTH: 52
<212> TYPE: DNA
<213> ORGANISM: Artificial Sequence
<220> FEATURE:
<223> OTHER INFORMATION: Synthetic

<400> SEQUENCE: 6
aaaagcagag agagcttccc tgaaagagat gactcctgga gcctacagta ct          52

<210> SEQ ID NO 7
<211> LENGTH: 30
<212> TYPE: DNA
<213> ORGANISM: Artificial Sequence
<220> FEATURE:
<223> OTHER INFORMATION: Synthetic

<400> SEQUENCE: 7
ttgcacggcg gtcactggac acagataact                                   30

<210> SEQ ID NO 8
<211> LENGTH: 27
<212> TYPE: DNA
<213> ORGANISM: Artificial Sequence
<220> FEATURE:
<223> OTHER INFORMATION: Synthetic

<400> SEQUENCE: 8
caagcggctc cgggcagaaa gggttca                                      27
```

ADENO-ASSOCIATED VIRUS MEDIATED DELIVERY OF C1E1 AS A THERAPY FOR ANGIOEDEMA

CROSS-REFERENCE TO RELATED APPLICATIONS

This patent application claims the benefit of U.S. Provisional Patent Application No. 62/167,603 filed on May 28, 2015 and U.S. Provisional Patent Application No. 62/324,183 filed Apr. 18, 2016, which are hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 42,664 Byte ASCII (Text) file named "724068 ST25-Replacement.txt," created on Jul. 12, 2018.

BACKGROUND OF THE INVENTION

Hereditary angioedema (HAE) is a rare and potentially life-threatening genetic condition characterized by recurrent episodes of swelling that most often affect the skin or mucosal tissues of the upper respiratory and gastrointestinal tracts (see e.g., Banerji, *Ann Allergy Asthma Immunol*, 111: 329-336 (2013) and Aygoren-Pursun et al., *Orphanet J Rare Dis.*, 9: 99 (2014)). The disease is inherited in an autosomal dominant pattern and affects 1:10,000 to 1:50,000 people. The underlying cause of HAE (type I and II) is attributed to autosomal dominant inheritance of mutations in the C1 esterase inhibitor gene (C1EI gene or SERPING1 gene), mapped to chromosome 11. Eighty-five percent of HAE cases are type I in which there is a deficiency in the amount of C1 esterase inhibitor produced (see e.g., Gower et al., *World Allergy Organ J.*, 4: S9-S21 (2011); Cungo et al., *Trends Mol Med*, 15: 69-78 (2009); Gooptu et al., *Annu Rev Biochem*, 78: 147-176 (2009); and Zuraw et al., *J Allergy Clin Immunol Pract*, 1: 458-467 (2013)). The remainder of cases are characterized by the expression of a dysfunctional C1 esterase inhibitor.

The frequency, duration and severity of attacks associated with HAE vary, with 30% of patients reporting a frequency of greater than one attack/month, 40% report 6 to 11 attacks/year and the remaining 30% are infrequently symptomatic. Usually, symptoms are transient progressing over 12 to 36 hours and subsiding within 2 to 5 days; however, some attacks may last up to one week. Although HAE episodes are self-limiting, the unpredictable occurrence of attacks places considerable strain on patients, often heavily impacting quality of life, and can be fatal.

To date, therapeutic agents are indicated for long-term prophylaxis, therapy for acute attacks and short-term prophylaxis (i.e., prior to dental surgery), and include agents such as Danazol, which has a high adverse effect profile, C1 inhibitor replacement protein, bradykinin receptor antagonists, kallikrein inhibitors, fresh frozen plasma and purified C1 inhibitor. These therapies can alleviate symptoms and maximize quality of life; however, disease recurrence and the need for long-term continued administration remains a major obstacle to therapy (see e.g., Aberer, *Ann Med*, 44: 523-529 (2012); Charignon et al., *Expert Opin Pharmacother*, 13: 2233-2247 (2012); Papadopoulou-Alataki, *Curr Opin Allergy Clin Immunol*, 10: 20-25 (2010); Parikh et al., *Curr Allergy Asthma Rep*, 11: 300-308 (2011); Tourangeau et al., *Curr Allergy Asthma Rep*, 11: 345-351 (2011); Bowen et al., *Ann Allergy Asthma Immunol*, 100: S30-S40 (2008); Frank, *Immunol Allergy Clin North Am*, 26: 653-668 (2006); Cicardi et al., *J Allergy Clin Immunol*, 99: 194-196 (1997); Kreuz et al., *Transfusion* 49: 1987-1995 (2009); Bork et al., *Ann Allergy Asthma Immunol*, 100: 153-161 (2008); and Cicardi et al., *J Allergy Clin Immunol*, 87: 768-773 (1991)).

Thus, there is a need for a novel long-lasting therapeutic approach to treat angioedema associated with C1 esterase inhibitor deficiency. This invention provides such a therapeutic approach to treat angioedema.

BRIEF SUMMARY OF THE INVENTION

The invention provides a vector comprising a promoter operably linked to a nucleic acid sequence which encodes human C1 esterase inhibitor (C1EI) or a nucleic acid sequence which encodes Factor XII. This invention also provides a composition comprising the vector and a method of using the vector to treat a deficiency in a plasma C1 esterase inhibitor in a mammal, or to treat or prevent any symptom thereof. In addition, provided herein is a recombinant mouse that models human hereditary angioedema, the recombinant mouse comprising a mutation of SERPING1 that reduces C1EI activity in the mouse as compared to the same type of mouse without the SERPING1 mutation.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

FIG. 2B is a graph illustrating bradykinin levels in wild-type and S63 SERPING1$^{+/-}$ heterozygous mice. Mutant S63 and wild-type bradykinin levels were measured by ELISA.

Figure 4B:
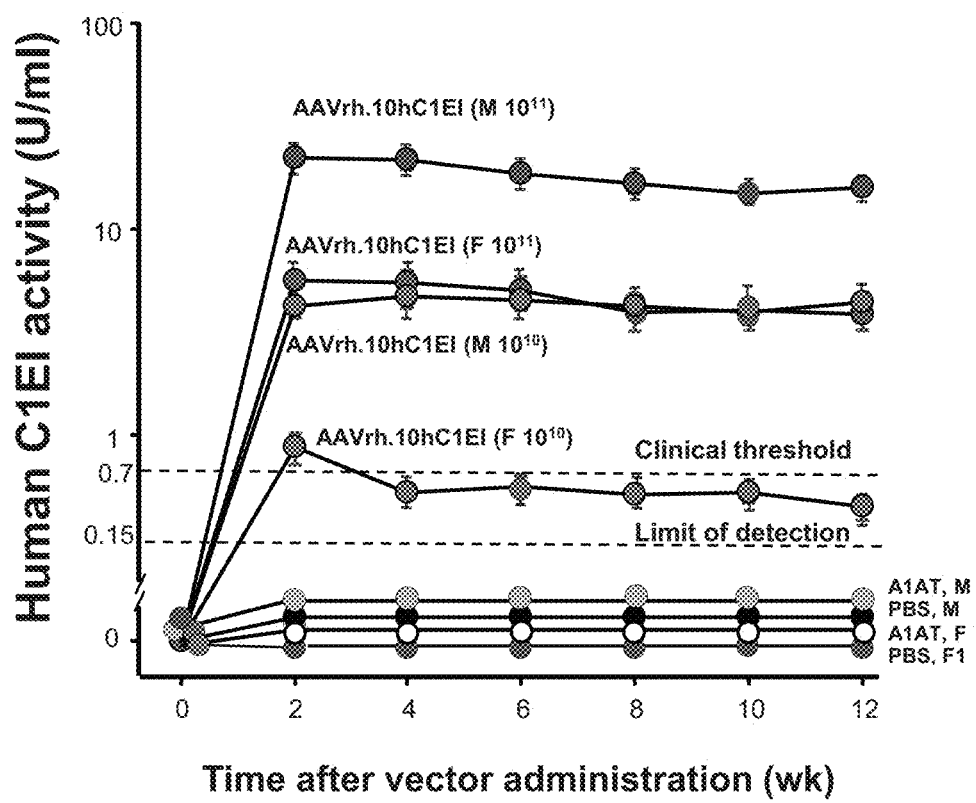
FIG. 4A is a graph of experimental data illustrating the long term expression of human C1EI following a single intravenous administration of the AAVrh.10hC1EI vector to wild-C57Bl/6Albino mice (n=5/group).

FIGS. 4B, 4C, and 4D are graphs of experimental data illustrating the dose dependent long term expression of human C1EI following single intravenous administration of $10^{10}$ gc AAVrh.10hC1EI, $10^{11}$ gc AAVrh.10hC1EI, $10^{11}$ AAVrh.10hα1AT (control), or PBS to C57Bl/6Albino (FIG. 4B), C57Bl/6 (FIG. 4C) mice (n=4-5 mice/group), or S63 (FIG. 4D) mice.

FIGS. 5A, 5B, and 5C are graphs of experimental data illustrating the long term expression of human C1EI following a single intravenous administration of $10^{11}$ gc AAV8hC1EI (FIG. 5A), AAV9hC1EI (FIG. 5B), or AAVrh.10hC1EI (FIG. 5C) to C57/Bl/6 mice (n=5 males/group, n=5 females/group, administration of PBS served as a control).

Figure 5D:
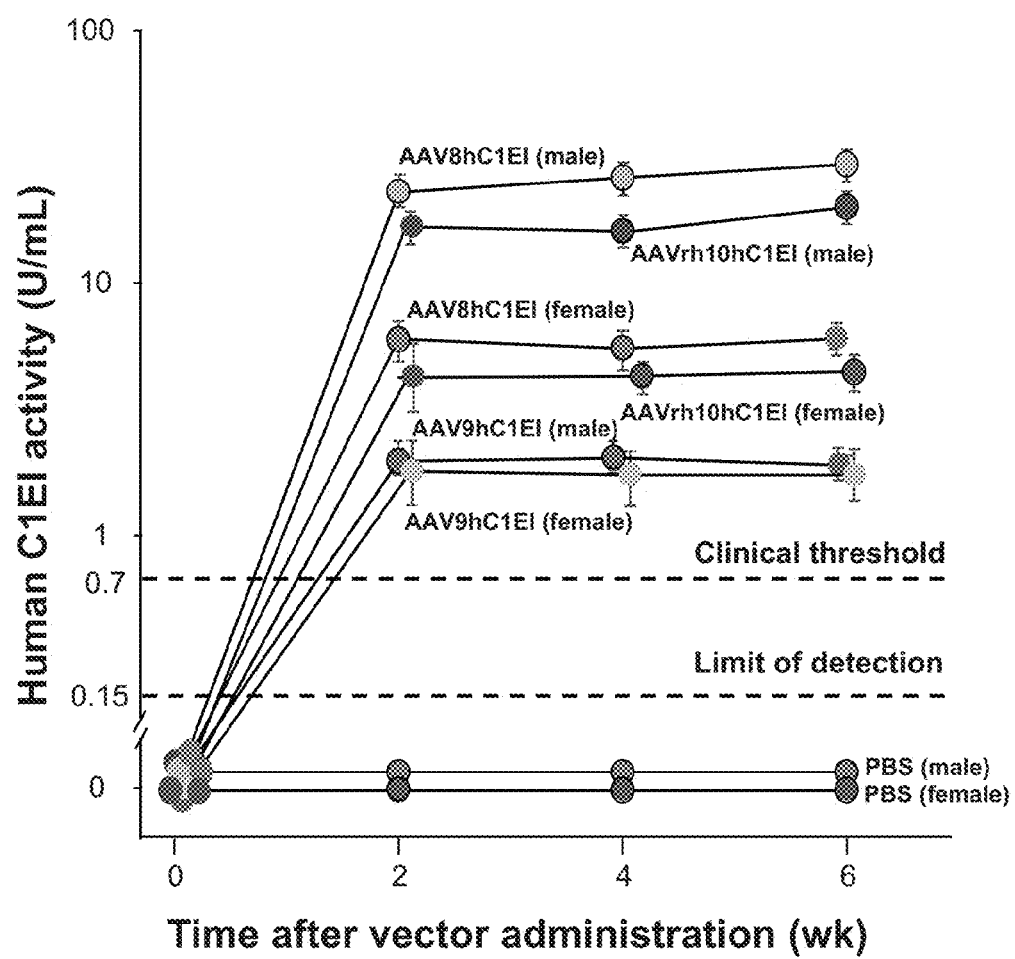

FIG. 5D is a graph of the combined data from FIGS. 5A-5C.

FIG. 6 is a graph of experimental data illustrating the changes in human C1EI activity two weeks following a single administration of AAVrh.10hC1EI in S63 and control wild-type B6(Cg)-Tyr$^{c-2J}$/J mice (S63 mice: n=4 males/group, n=4 females/group; B6(Cg)-Tyr$^{c-2J}$/J mice: n=4 males/group, n=4 females/group).

Figure 7A:
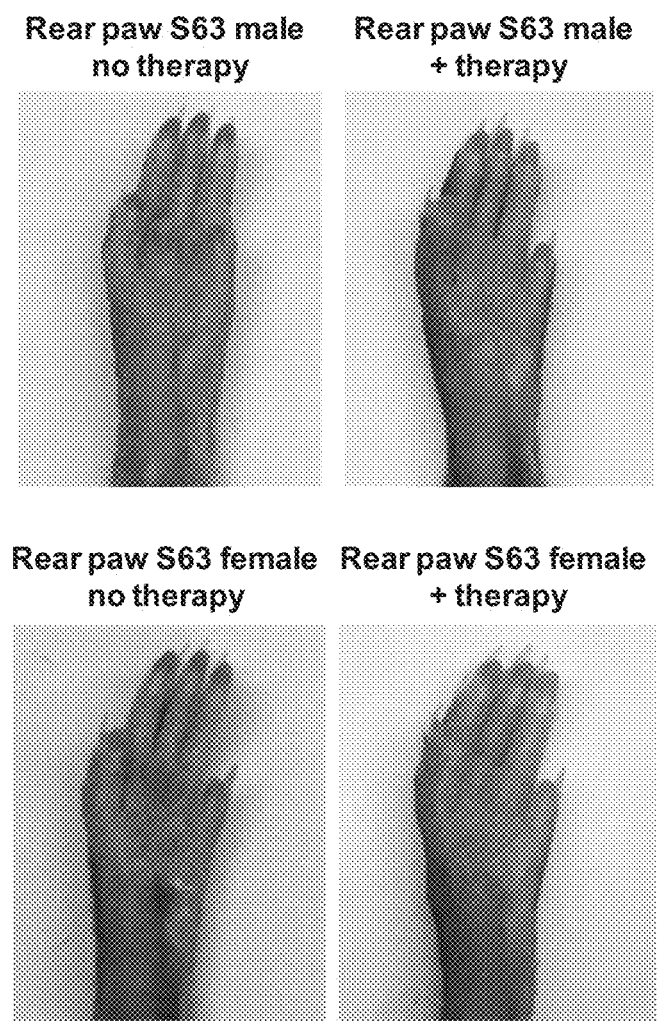
Figure 7B:
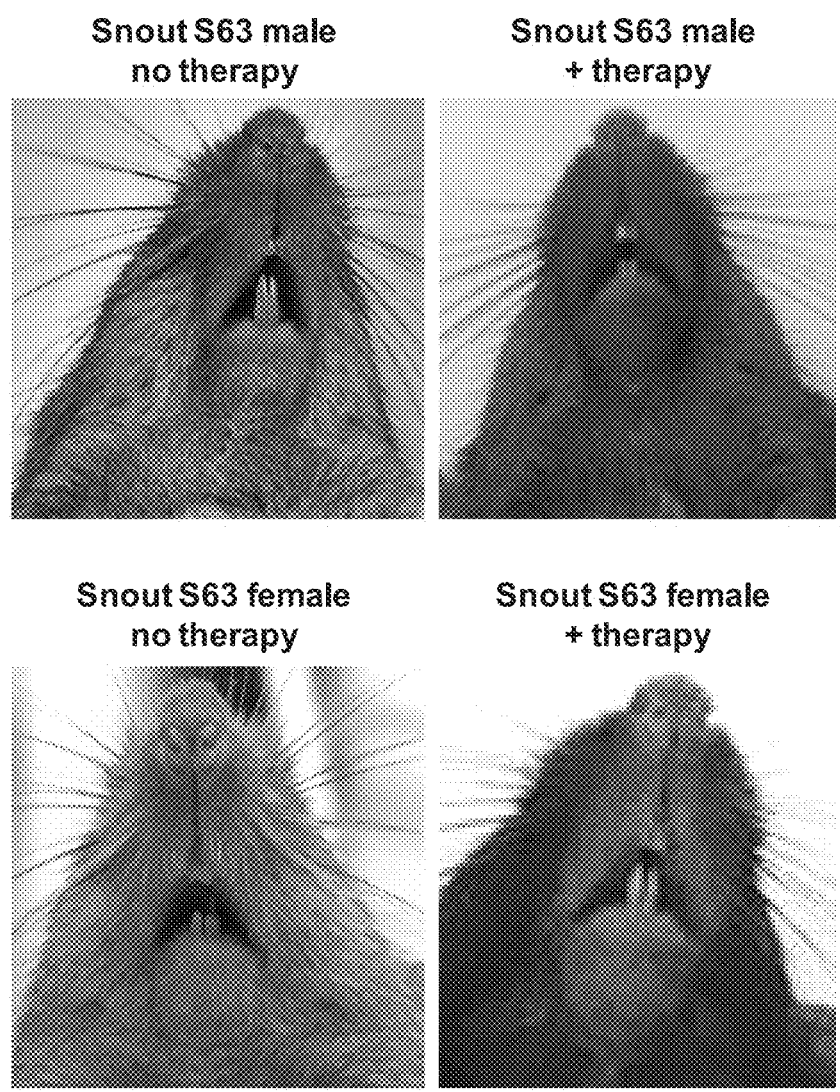

FIGS. 7A and 7B depict the effect of treatment of S63 SERPING1$^{+/-}$ mice with AAVrh.10hC1EI. Two weeks after S63 SERPING1$^{+/-}$ mice were administered AAVrh.10hC1EI Evans blue dye was administered by tail vein injection and after 30 minutes mice were photographed. FIG. 7A depicts the blue dye in the hind paws of S63 heterozygous untreated mice and S63 heterozygous AAVrh.10hC1EI treated mice (n=4 male, n=4 female). FIG. 7B depicts the blue dye in the snouts of S63 heterozygous untreated mice and S63 heterozygous AAVrh.10hC1EI treated mice (n=4 male, n=4 female).

Figure 8A:
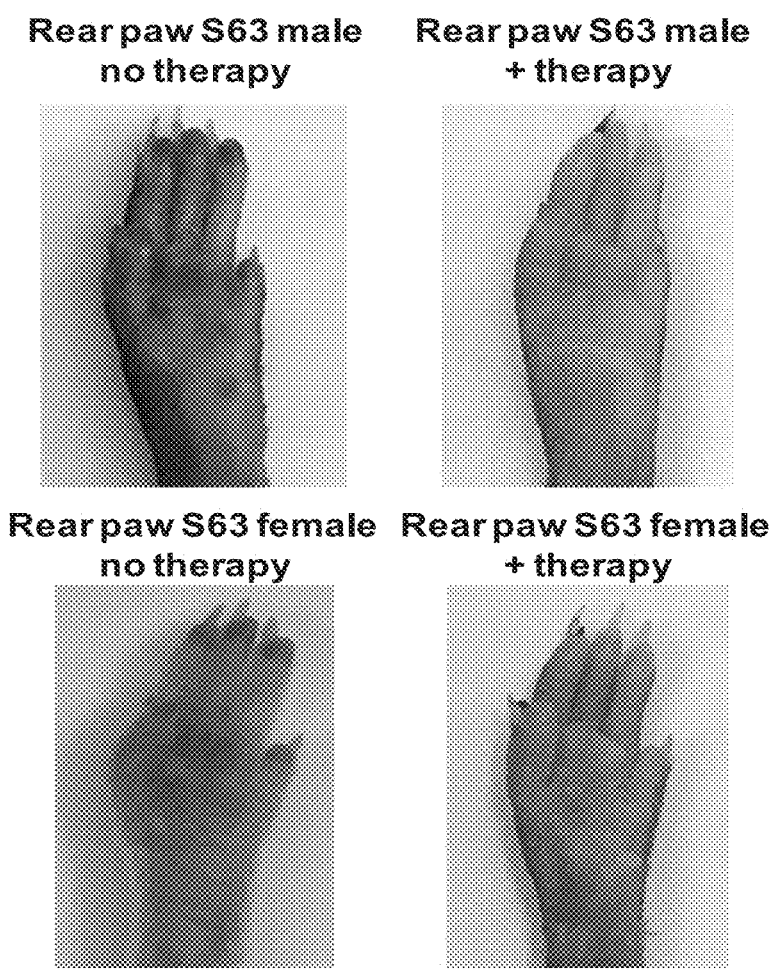

FIGS. 8A and 8B depict the effect of treatment of S63 SERPING1$^{+/-}$ mice with AAVrh.10hC1EI. Six weeks after S63 SERPING1$^{+/-}$ mice were administered AAVrh.10hC1EI Evans blue dye was administered by tail vein injection and after 30 minutes mice were photographed. FIG. 8A depicts the blue dye in the hind paws of S63 heterozygous untreated mice and S63 heterozygous AAVrh.10hC1EI treated mice (n=4 male, n=4 female). FIG. 8B depicts the blue dye in the snouts of S63 heterozygous untreated mice and S63 heterozygous AAVrh.10hC1EI treated mice (n=4 male, n=4 female).

FIGS. 9A-9F are graphs of experimental results of the quantitative weight of dye of the vascular permeability response of SERPING1$^{+/-}$ S63 AAVrh.10hC1EI treated and AAVrh.10hC1EI untreated mice (n=5/group) in the hind paw (FIG. 9A), kidney (FIG. 9B), intestines (FIG. 9C), lung (FIG. 9D), spleen (FIG. 9E), and heart (FIG. 9F).

Figure 10:
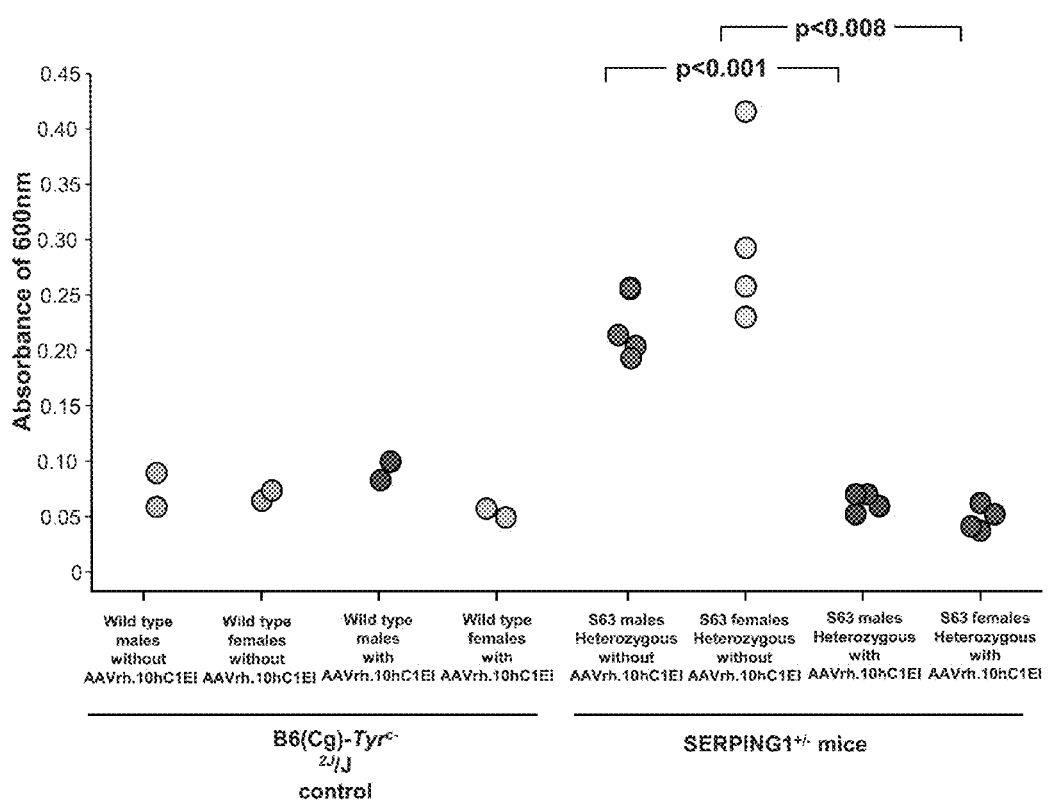

FIG. 10 is a graph of experimental results showing the spectrophotometric analysis of the vascular permeability response of SERPING1$^{+/-}$ S63 untreated mice (n=4 females, n=4 males) and S63 SERPING1$^{+/-}$ AAVrh.10hC1EI treated mice (n=4 females, n=4 males). B6(Cg)-Tyr$^{c-2J}$/J wild-type treated and untreated mice served as controls (n=2 females, n=2 males).

DETAILED DESCRIPTION OF THE INVENTION

The invention is predicated, at least in part, upon the ability of vectors to be safely administered to humans and to provide persistent expression of a therapeutic transgene. The invention provides a vector which comprises, consists essentially of, or consists of a promoter operably linked to a nucleic acid sequence that encodes human C1 esterase inhibitor (C1EI) or a nucleic acid sequence that encodes Factor XII. When the inventive vector consists essentially of a promoter operably linked to a nucleic acid sequence that encodes human C1EI or a nucleic acid sequence that encodes Factor XII, additional components can be included that do not materially affect the vector (e.g., genetic elements such as poly(A) sequences or restriction enzyme sites that facilitate manipulation of the vector in vitro). When the vector consists of a promoter operably linked to a nucleic acid sequence that encodes human C1EI or a nucleic acid sequence that encodes Factor XII, the vector does not comprise any additional components (i.e., components that are not endogenous to the vector and are not required to effect expression of the nucleic acid sequence to thereby provide the protein).

The vector of the invention can comprise, consist essentially of, or consist of any gene transfer vector known in the art. Examples of such vectors include adeno-associated viral (AAV) vectors, adenoviral vectors, lentiviral vectors, retroviral vectors, and plasmids. In a preferred embodiment the vector is an AAV vector.

Adeno-associated virus is a member of the Parvoviridae family and comprises a linear, single-stranded DNA genome of less than about 5,000 nucleotides. AAV requires co-infection with a helper virus (i.e., an adenovirus or a herpes virus), or expression of helper genes, for efficient replication. AAV vectors used for administration of therapeutic nucleic acids typically have approximately 96% of the parental genome deleted, such that only the terminal repeats (ITRs), which contain recognition signals for DNA replication and packaging, remain. This eliminates immunologic or toxic side effects due to expression of viral genes. In addition, delivering specific AAV proteins to producing cells enables integration of the AAV vector comprising AAV ITRs into a specific region of the cellular genome, if desired (see, e.g., U.S. Pat. Nos. 6,342,390 and 6,821,511). Host cells comprising an integrated AAV genome show no change in cell growth or morphology (see, for example, U.S. Pat. No. 4,797,368).

The AAV ITRs flank the unique coding nucleotide sequences for the non-structural replication (Rep) proteins and the structural capsid (Cap) proteins (also known as virion proteins (VPs)). The terminal 145 nucleotides are self-complementary and are organized so that an energetically stable intramolecular duplex forming a T-shaped hairpin may be formed. These hairpin structures function as an origin for viral DNA replication by serving as primers for the cellular DNA polymerase complex. The Rep genes encode the Rep proteins Rep78, Rep68, Rep52, and Rep40. Rep78 and Rep68 are transcribed from the p5 promoter, and Rep 52 and Rep40 are transcribed from the p19 promoter. The Rep78 and Rep68 proteins are multifunctional DNA binding proteins that perform helicase and nickase functions during productive replication to allow for the resolution of AAV termini (see, e.g., Im et al., *Cell*, 61: 447-57 (1990)). These proteins also regulate transcription from endogenous AAV promoters and promoters within helper viruses (see, e.g., Pereira et al., *J. Virol.*, 71: 1079-1088 (1997)). The other Rep proteins modify the function of Rep78 and Rep68. The cap genes encode the capsid proteins VP1, VP2, and VP3. The cap genes are transcribed from the p40 promoter.

The inventive AAV vector can be generated using any AAV serotype known in the art. Several AAV serotypes and over 100 AAV variants have been isolated from adenovirus stocks or from human or nonhuman primate tissues (reviewed in, e.g., Wu et al., *Molecular Therapy*, 14(3): 316-327 (2006)). Generally, the AAV serotypes have genomic sequences of significant homology at the nucleic acid sequence and amino acid sequence levels, such that different serotypes have an identical set of genetic functions, produce virions which are essentially physically and functionally equivalent, and replicate and assemble by practically identical mechanisms. AAV serotypes 1-6 and 7-9 are defined as "true" serotypes, in that they do not efficiently cross-react with neutralizing sera specific for all other existing and characterized serotypes. In contrast, AAV serotypes 6, 10 (also referred to as Rh10), and 11 are considered "variant" serotypes as they do not adhere to the definition of a "true" serotype. AAV serotype 2 (AAV2) has been used extensively for gene therapy applications due to its lack of pathogenicity, wide range of infectivity, and ability to establish long-term transgene expression (see, e.g., Carter, B. J., *Hum. Gene Ther.*, 16: 541-550 (2005); and Wu et al., supra). Genome sequences of various AAV serotypes and comparisons thereof are disclosed in, for example, GenBank Accession numbers U89790, J01901, AF043303, and AF085716; Chiorini et al., *J. Virol.*, 71: 6823-33 (1997); Srivastava et al., *J. Virol.*, 45: 555-64 (1983); Chiorini et al., *J. Virol.*, 73: 1309-1319 (1999); Rutledge et al., *J. Virol.*, 72: 309-319 (1998); and Wu et al., *J. Virol.*, 74: 8635-47 (2000)).

AAV rep and ITR sequences are particularly conserved across most AAV serotypes. For example, the Rep78 proteins of AAV2, AAV3A, AAV3B, AAV4, and AAV6 are reportedly about 89-93% identical (see Bantel-Schaal et al., *J. Virol.*, 73(2): 939-947 (1999)). It has been reported that AAV serotypes 2, 3A, 3B, and 6 share about 82% total nucleotide sequence identity at the genome level (Bantel-Schaal et al., supra). Moreover, the rep sequences and ITRs of many AAV serotypes are known to efficiently cross-complement (i.e., functionally substitute) corresponding sequences from other serotypes during production of AAV particles in mammalian cells.

Generally, the cap proteins, which determine the cellular tropicity of the AAV particle, and related cap protein-encoding sequences, are significantly less conserved than Rep genes across different AAV serotypes. In view of the ability of Rep and ITR sequences to cross-complement corresponding sequences of other serotypes, the AAV vector can comprise a mixture of serotypes and thereby be a "chimeric" or "pseudotyped" AAV vector. A chimeric AAV vector typically comprises AAV capsid proteins derived from two or more (e.g., 2, 3, 4, etc.) different AAV serotypes. In contrast, a pseudotyped AAV vector comprises one or more ITRs of one AAV serotype packaged into a capsid of another AAV serotype. Chimeric and pseudotyped AAV vectors are further described in, for example, U.S. Pat. No. 6,723,551; Flotte, *Mol. Ther.*, 13(1): 1-2 (2006); Gao et al., *J. Virol.*, 78: 6381-6388 (2004); Gao et al., *Proc. Natl. Acad. Sci. USA*, 99: 11854-11859 (2002); De et al., *Mol. Ther.*, 13: 67-76 (2006); and Gao et al., *Mol. Ther.*, 13: 77-87 (2006).

In one embodiment, the AAV vector is generated using an AAV that infects humans (e.g., AAV2). In a preferred embodiment the AAV vector generated using an AAV that infects humans is AAV8 or AAV9. Alternatively, the AAV vector is generated using an AAV that infects non-human primates, such as, for example, the great apes (e.g., chimpanzees), Old World monkeys (e.g., macaques), and New World monkeys (e.g., marmosets). Preferably, the AAV vector is generated using an AAV that infects a non-human primate pseudotyped with an AAV that infects humans. Examples of such pseudotyped AAV vectors are disclosed in, e.g., Cearley et al., *Molecular Therapy*, 13: 528-537 (2006). In one embodiment, an AAV vector can be generated which comprises a capsid protein from an AAV that infects rhesus macaques pseudotyped with AAV2 inverted terminal repeats (ITRs). In a particularly preferred embodiment, the inventive AAV vector comprises a capsid protein from AAV10 (also referred to as "AAVrh.10"), which infects rhesus macaques pseudotyped with AAV2 ITRs (see, e.g., Watanabe et al., *Gene Ther.*, 17(8): 1042-1051 (2010); and Mao et al., *Hum. Gene Therapy*, 22: 1525-1535 (2011)).

The inventive vector comprises a promoter operably linked to a nucleic acid sequence that encodes human C1EI or a nucleic acid sequence that encodes Factor XII. DNA regions are "operably linked" when they are functionally related to each other. A promoter is "operably linked" to a coding sequence if it controls the transcription of the sequence.

A "promoter" is a region of DNA that initiates transcription of a particular gene. A large number of promoters from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction).

The promoter of the inventive vector can comprise, consist essentially of, or consist of any promoter known in the art. Examples of classes of such promoters include constitutively active promoters (e.g., human beta-actin, chicken beta-actin, cytomegalovirus (CMV), and SV40), cell type specific promoters (e.g., CD19 gene promoter, CaMKIIa, and UAS), or an inducible promoter (e.g., the Tet system (U.S. Pat. Nos. 5,464,758 and 5,814,618), the Ecdysone inducible system (No et al., *Proc. Natl. Acad. Sci.*, 93: 3346-3351 (1996)), the T-REX™ system (Invitrogen, Carlsbad, Calif.), the Cre-ERT tamoxifen inducible recombinase system (Indra et al., *Nuc. Acid. Res.*, 27: 4324-4327 (1999); *Nuc. Acid. Res.*, 28: e99 (2000); U.S. Pat. No. 7,112,715; and Kramer & Fussenegger, *Methods Mol. Biol.*, 308: 123-144 (2005)), and the LACSWITCH™ System (Stratagene, San Diego, Calif.)).

In a preferred embodiment of the invention the promoter is a constitutively active promoter, an inducible promoter, or a cell-type specific promoter. In a more preferred embodiment of the invention the promoter is a constitutively active promoter, and preferably the constitutively active promoter is the chicken beta-actin promoter.

"Nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides.

The nucleic acid sequence operably linked to the promoter of the inventive vector may comprise any nucleic acid sequence that encodes a therapeutic gene which inhibits or reduces submucosal or subcutaneous edema in a mammal with hereditary angioedema. The nucleic acid sequence preferably encodes human C1EI or Factor XII. Preferably the nucleic acid sequence encodes for the full length human C1EI protein; however, the nucleic acid sequence may also encode variants, such as truncations, as long as the protein produced maintains the functional characteristics of the full length protein (e.g., inhibition of the complement system). The nucleic acid sequence may also encode for fusion proteins which are comprised of an active protein e.g., human C1EI, Factor XII, or any therapeutic gene which inhibits or reduces submucosal or subcutaneous edema in a mammal with hereditary angioedema and a second moiety, usually a protein, which improves the properties (e.g., efficacy, solubility, or half-life) of the active protein. Examples of the second moiety are known in the art and include, for example, the Fc domain of an immunoglobulin and polyethylene glycol (PEG).

C1EI is a protease inhibitor that circulates in the plasma at levels around 21-40 mg/kg. One of the main functions of C1EI is the inhibition of the complement system to prevent spontaneous activation by binding to and inactivating the C1r and C1s proteases of the classical complement pathway. Human C1EI comprises a heavily glycosylated single-chain polypeptide of 500 amino acid residues and is normally produced by hepatocytes, fibroblasts, monocytes, and endothelial cells. Human C1EI is encoded by the SERPING1 gene which is located on chromosome 11 at 11q11-q13.1. Chromosome 11q11-q13.1 is roughly 1.5 kilobases long and encompasses 8 coding exons. The amino acid sequence and nucleic acid sequence of human C1EI as, well as function variants of human C1EI, are well known in the art. An example of the amino acid sequence of a C1EI protein and nucleotide sequence encoding a C1E1 protein can be found at, for example, GenBank Accession number: AAM21515.1 (amino acid) (SEQ ID NO: 1) and AF435921.1 (nucleic acid) (SEQ ID NO: 2).

Factor XII is a coagulation factor that circulates in the plasma and is associated with hereditary angioedema type III. Factor XII functions in the blood clotting cascade by interacting with coagulation factor XI and also plays a role in stimulating inflammation. Factor XII is encoded by the F12 gene. The amino acid sequence and nucleic acid sequence of Factor XII as, well as function variants of Factor XII, are well known in the art and can be found at, for example, GenBank Accession number: AAB59490.1 (amino acid) (SEQ ID NO: 3) and M11723.1 (nucleic acid) (SEQ ID NO: 4).

The nucleic acid sequence encoding the human C1EI or Factor XII, can be generated using methods known in the art. For example, nucleic acid sequences, polypeptides, and proteins can be recombinantly produced using standard recombinant DNA methodology (see, e.g., Sambrook et al., *Molecular Cloning: A Laboratory Manual*, 3$^{rd}$ ed., Cold Spring Harbor Press, Cold Spring Harbor, N.Y., 2001; and Ausubel et al., *Current Protocols in Molecular Biology*, Greene Publishing Associates and John Wiley & Sons, NY, 1994). Further, a synthetically produced nucleic acid sequence encoding human C1EI or Factor XII, can be isolated and/or purified from a source, such as a bacterium, an insect, or a mammal, e.g., a rat, a human, etc. Methods of isolation and purification are well-known in the art. Alternatively, the nucleic acid sequences described herein can be commercially synthesized. In this respect, the nucleic acid sequence can be synthetic, recombinant, isolated, and/or purified. The sequences (e.g., SEQ ID NOs: 1-4) can further be optimized for increased mRNA stability and to reduce the possibility of trans-inhibition by the mutant mRNA.

In addition to the promoter operably linked to a nucleic acid sequence encoding human C1EI or Factor XII, the vector preferably comprises additional expression control sequences, such as enhancers, polyadenylation signals, transcription terminators, internal ribosome entry sites (IRES), and the like, that provide for the expression of the nucleic acid sequence in a host cell. Exemplary expression control sequences are known in the art and described in, for example, Goeddel, *Gene Expression Technology: Methods in Enzymology*, Vol. 185, Academic Press, San Diego, Calif. (1990).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The nucleic acid sequence encoding the human C1EI or Factor XII may be operably linked to a CMV enhancer/chicken β-actin promoter (also referred to as a "CAG promoter") (see, e.g., Niwa et al., *Gene*, 108: 193-199 (1991); Daly et al., *Proc. Natl. Acad. Sci. U.S.A.*, 96: 2296-2300 (1999); and Sondhi et al., *Mol. Ther.*, 15: 481-491 (2007)).

The invention provides a composition comprising, consisting essentially of, or consisting of the above-described vector and a pharmaceutically acceptable (e.g. physiologically acceptable) carrier. When the composition consists essentially of the inventive vector and a pharmaceutically acceptable carrier, additional components can be included that do not materially affect the composition (e.g., adjuvants, buffers, stabilizers, anti-inflammatory agents, solubilizers, preservatives, etc.). When the composition consists of the inventive vector and the pharmaceutically acceptable carrier, the composition does not comprise any additional components. Any suitable carrier can be used within the context of the invention, and such carriers are well known in the art. The choice of carrier will be determined, in part, by the particular site to which the composition may be administered and the particular method used to administer the composition. The composition optionally can be sterile with the exception of the vector described herein. The composition can be frozen or lyophilized for storage and reconstituted in a suitable sterile carrier prior to use. The compositions can be generated in accordance with conventional techniques described in, e.g., *Remington: The Science and Practice of Pharmacy*, 21st Edition, Lippincott Williams & Wilkins, Philadelphia, Pa. (2001).

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the carrier is a buffered saline solution. More preferably, the inventive vector is administered in a composition formulated to protect the inventive vector from damage prior to administration. For example, the composition can be formulated to reduce loss of the vector on devices used to prepare, store, or administer the vector, such as glassware, syringes, or needles. The composition can be formulated to decrease the light sensitivity and/or temperature sensitivity of the vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the vector, facilitate administration, and increase the efficiency of the inventive method. Formulations for vector-containing compositions are further described in, for example, Wright et al., *Curr. Opin. Drug Discov. Devel.*, 6(2): 174-178 (2003) and Wright et al., *Molecular Therapy*, 12: 171-178 (2005))

The composition also can be formulated to enhance transduction efficiency. In addition, one of ordinary skill in the art will appreciate that the inventive vector can be present in a composition with other therapeutic or biologically-active agents. For example, factors that control inflammation, such as ibuprofen or steroids, can be part of the composition to reduce swelling and inflammation associated with in vivo administration of the vector. Antibiotics, i.e., microbicides and fungicides, can be present to treat existing infection and/or reduce the risk of future infection, such as infection associated with gene transfer procedures.

The invention provides a method of inhibiting or reducing submucosal or subcutaneous edema in a mammal with hereditary angioedema or a method of preventing or treating hereditary angioedema in a mammal comprising administering the inventive vector to the mammal, whereupon the nucleic is expressed to produce the protein that inhibits or reduces submucosal or subcutaneous edema or prevents or treats hereditary angioedema. In a preferred embodiment the mammal is a human.

Preventing or treating hereditary angioedema encompasses any degree of amelioration of any physiological response or symptom brought on by hereditary angioedema. Inhibiting or reducing submucosal or subcutaneous edema encompasses any degree of amelioration of submucosal or subcutaneous edema.

Any route of administration can be used to deliver the composition to the mammal. Indeed, although more than one route can be used to administer the composition, a particular route can provide a more immediate and more effective reaction than another route. Preferably, the composition is administered via intramuscular injection. A dose of composition also can be applied or instilled into body cavities, absorbed through the skin (e.g., via a transdermal patch), inhaled, ingested, topically applied to tissue, or administered parenterally via, for instance, intravenous, intraperitoneal, intraoral, intradermal, subcutaneous, or intraarterial administration.

The composition can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the AAV vector. The composition also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a poly-lactic-glycolic acid.

The dose of the vector in the composition administered to the mammal will depend on a number of factors, including the size (mass) of the mammal, the extent of any side-effects, the particular route of administration, and the like. Preferably, the inventive method comprises administering a "therapeutically effective amount" of the composition comprising the inventive vector described herein. A "therapeutically effective amount" refers to an amount effective, at dosages and for periods of time necessary, to achieve a desired therapeutic result. The therapeutically effective amount may vary according to factors such as the degree of allergen sensitivity, age, sex, and weight of the individual, and the ability of the vector to elicit a desired response in the individual.

In another embodiment, the inventive method can comprise administering a "prophylactically effective amount" of the composition comprising the inventive vector. A "prophylactically effective amount" refers to an amount effective, at dosages and for periods of time necessary, to achieve a desired prophylactic result (e.g., prevention of an immune response or allergic reaction). Subjects that are in need of prophylactic administration can be readily determined by routine testing known in the art. Additionally, subjects with a previous hereditary angioedema attack can be treated prophylactically against future attacks.

In a preferred embodiment of the invention, the composition is administered once to the mammal. It is believed that a single administration of the composition will result in persistent expression of human C1EI in the mammal with minimal side effects. However, in certain cases, it may be appropriate to administer the composition multiple times during a therapeutic or prophylactic treatment period and/or employ multiple administration routes, e.g., intramuscular and subcutaneous, to ensure sufficient exposure of cells to the composition. For example, the composition may be administered to the mammal two or more times (e.g., 2, 3, 4, 5, 6, 6, 8, 9, or 10 or more times) during a therapeutic or prophylactic treatment period.

The dose of vector in the composition required to achieve a particular therapeutic or prophylactic effect (i.e., reduction or inhibition of an allergic reaction) typically is administered in units of vector genome copies per cell (gc/cell) or vector genome copies/per kilogram of body weight (gc/kg). One of ordinary skill in the art can readily determine an appropriate vector dose range to treat a patient having a particular immune response based on these and other factors that are well known in the art.

The following examples further illustrate the invention but, of course, should not be construed as in any way limiting its scope.

EXAMPLE 1

This example demonstrates the development and characterization of a C1EI deficient mouse model of hereditary angioedema.

The C1EI deficient mouse model was developed using the clustered regularly interspaced short palindromic repeat (CRISPR) and CRISPR-associated endonuclease 9 (Cas9) technology targeting exon 3 (E3) of SERPING1. The Cas9 endonuclease is directed to generate site-specific DNA double-stranded breaks (DSB) when provided with a synthetic single-guide RNA (sgRNA) targeting the desired sequence. In mammalian cells, the DSB produced by the Cas9 cleavage are repaired by the cell non-homologous end joining (NHEJ) repair pathway that introduces insertion/deletion mutations (InDels) in the gene, which in turn cause frameshifts resulting in null alleles. We leveraged this technology to introduce targeted null mutations in the mouse SERPING1 gene.

F1 zygotes from CBA/J×B6/J mice were co-injected with a functional single guide RNA targeting exon 3 of SERPING1 and Cas9 mRNA. Embryos were implanted at the 2-cell stage into surrogate mothers and all pups were screened for presence of SERPING1 exon 3 insertion/deletions by T7 endonuclease I-based PCR analysis. Mice with InDels in exon 3 were selected for breeding and further DNA sequencing. Mice were bred as pairs (one female with one male) or trios (two females with one male); with B6(Cg)-Tyr$^{c-2J}$/J mice (B6 Albino mice, Jackson Laboratory, Bar Harbor, Me.). All mice were housed in microisolator cages and maintained according to standard guidelines.

All first generation pups were screened for exon 3 mutations by T7 endonuclease I digestion. Briefly, mouse genomic DNA was extracted from tail tissue (0.5 cm, tail tip) and exon 3 was amplified by PCR using primers flanking the mutation target region (forward primer, 5'-TTGCACGGCG-GTCACTGGACACAGATAACT-3' (SEQ ID NO: 7); reverse primer, 5'-CAAGCGGCTCCGGGCA-GAAAGGGTTCA-3' (SEQ ID NO: 8)). PCR products were then denatured at high temperature, re-annealed for DNA duplex formation, and digested using T7 endonuclease I (T7E-I), which cleaves mismatched DNA duplexes (heteroduplexes). Digestion by T7EI of mutation carrying heteroduplexes results in two or more smaller DNA fragments that can be resolved by agarose gel electrophoresis.

Founder heterozygous mice carrying mutations in exon 3 were selected for genomic DNA sequencing. Tail tip tissue (0.5 cm) was obtained from SERPING1 knockout mice anesthetized under isoflurane gas, and genomic DNA (gDNA) extracted using KAPA Express Extract DNA Extraction Kit (KAPA Biosytems; Wilmington, MA). Genomic DNA was amplified using specific primers that flanked the targeted exon 3 region of the SERPING1 gene (forward primer, 5'-TTGCACGGCGGTCACTGGACACA-GATAACT-3' (SEQ ID NO: 7); reverse primer, 5'-CAAGCGGCTCCGGGCAGAAAGGGTTCA-3' (SEQ ID NO: 8)). PCR amplification was performed with Taq polymerase and reagents supplied by KAPA2G Fast (Hot-Start) Genotyping Mix (KAPA Biosytems; Wilmington, MA). Each cycle of denaturation (95° C., 30 sec), annealing (60° C., 30 sec), and extension (72° C., 30 sec) was repeated 35 times. The resultant PCR product was purified using QIAGEN PCR Purification Kit (QIAGEN; Valencia, CA), the DNA eluted in 50 µl buffer EB, and cloned into a TOPO vector for DNA sequencing (Life Technologies, Norwalk, CT). Multiple TOPO clones for each mutant were sequenced by Sanger technology to identify the mutation introduced by the CRISPR/Cas9-directed NHEJ DNA repair system.

Figure 1:
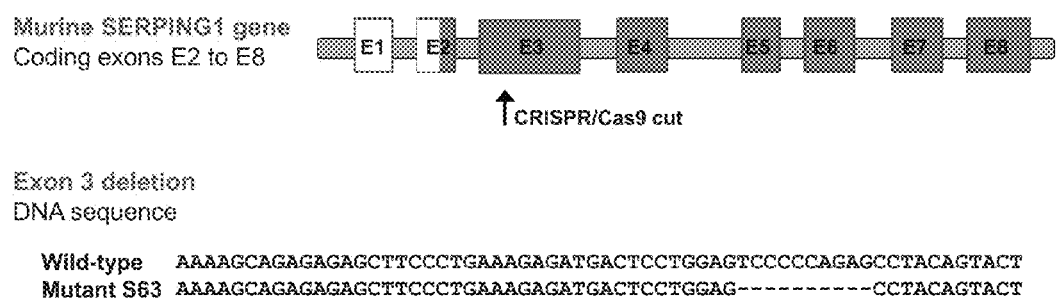
FIG. 1 is a schematic of the method used to generate the S63 mouse model of C1EI deficiency generated with SERPING1 E3 targeted mutations. The wild-type and mutant S63 DNA sequences correspond to SEQ ID NOs: 5 and 6, respectively.

Using this technology, we have generated a number of mice with different genetic variants in exon 3 of the SERPING1 gene (FIG. 1). One of these mice (referred to as "S63") has been characterized in detail and used as a model of hereditary angioedema for the demonstration of efficacy of the AAVrh.10hC1EI therapy. The S63 mice appeared normal at birth, and subsequently developed and bred normally.

Murine C1EI (mC1EI) levels were evaluated in the S63 mouse sera by ELISA (Biomatik, Wilmington, Del.) according to manufacturer's instructions. Murine bradykinin levels were evaluated in the S63 mouse sera by ELISA (MyBioSource, San Diego, Calif.) according to manufacturer's instructions. Human C1EI (hC1EI) activity levels were evaluated by a chromogenic activity assay that measures the ability of the protein to inhibit its natural substrate, C1 esterase (TECHNOCHROM® C1-INH [CE], DiaPharma Group, West Chester, Ohio). In brief, the assay is based on the inhibition of C1 esterase activity. C1 esterase cleavage of substrate C1-1(C2H5CO-lys (ε-Cbo)-Gly-Arg-pNA) releases the chromophore para-nitroaniline (pNA). The absorbance of released pNA is measured at OD 405 nm and is inversely proportional to the concentration (activity) of C1 esterase inhibitor present in the serum or plasma. The activity assay was conducted per the manufacturer's protocol, and results expressed as a unit of function (U/mL). All analyses were performed in duplicate. Evans blue dye (30 mg/kg in 100 µl phosphate buffered saline; Sigma Chemical Co., St. Louis, Mo.) was injected into the tail vein of 6 to 8 weeks old mice. Photographs of hind-paws and snouts were taken 30 min after injection of Evans blue dye. After the mice were euthanized by CO2 inhalation, paws were removed, blotted dry, and weighed. The Evans blue dye was extracted (equal weights) with 1 ml of formamide overnight at 55° C. and measured spectrophotometrically at 600 nm.

Figure 2A:
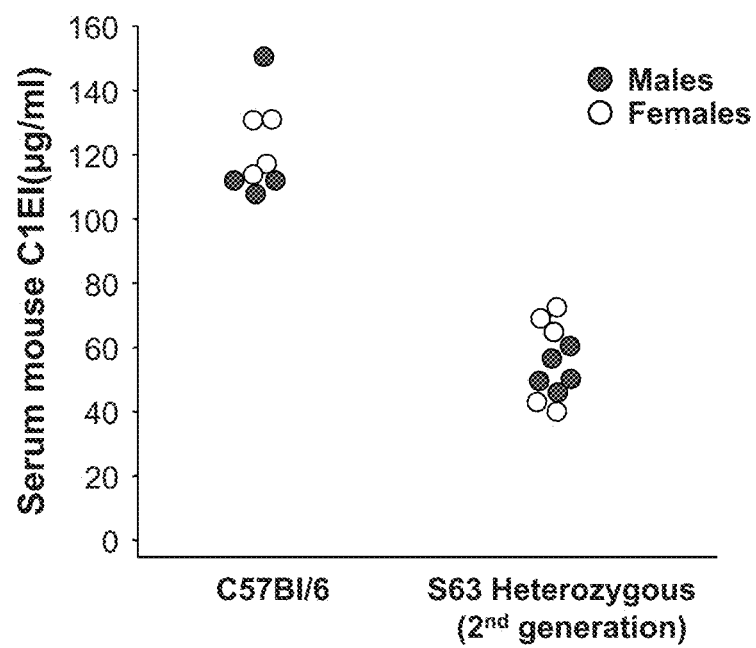
FIG. 2A is a graph illustrating the level of C1EI in wild-type and S63 SERPING1$^{+/-}$ heterozygous mice. Mutant S63 and wild-type C1EI levels were measured by ELISA.

The results from these studies indicate that the level of C1EI in the S63 mice was markedly lower than the C1EI level in the wild-type controls (FIG. 2A) and bradykinin levels were elevated in S63 mice compared to wild-type controls (FIG. 2B). Indicating that the S63 mouse model provides an in vivo animal model of hereditary angioedema.

EXAMPLE 2

This example demonstrates the design and in vitro characterization of the AAV-vector comprising a promoter operably linked to a nucleic acid sequence encoding human C1EI.

Figure 3A:
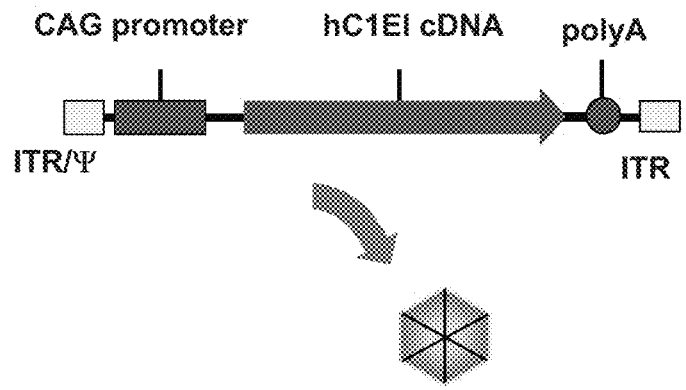
FIG. 3A is a schematic of the AAVrh.10hC1EI, AAV8hC1EI, or AAV9hC1EI vector, which depicts the AAV2 inverted terminal repeats (ITR), encapsidation signal (ψ), CMV enhancer/chicken beta-actin (CAG) promoter, optimized human C1EI (hC1EI) cDNA, and rabbit β-globulin polyadenylation signal.

The expression cassette consists of the AAV2 inverted terminal repeats (ITR), encapsidation signal (ψ), cytomegalovirus (CMV) enhancer chicken-β-actin promoter (CAG promoter) operably linked to human C1EI cDNA sequence and the rabbit β-globin polyadenylation signal (FIG. 3A). The hC1EI cDNA sequence was optimized for increased mRNA stability and to reduce the possibility of trans-inhibition by the mutant mRNA. hC1EI cDNA was sequence-optimized using human-biased codons and removal of: mRNA instability elements; low (<30%) or rich (>80%) GC regions; translation initiation sequences within the coding region; and potential splicing signals. Optimized hC1EI cDNA was synthesized with an optimal Kozak consensus.

The optimized full length human C1EI cDNA sequence was synthesized and cloned into the pAAV plasmid-under control of the CAG promoter. The AAV-hC1EI plasmid was produced by co-transfection into human embryonic kidney 293T cells (HEK 293T; American Type Culture Collection) of the pAAV plasmid together with a plasmid carrying the AAV Rep proteins derived from AAV2 needed for vector replication, the AAVrh.10 viral structural (Cap) proteins VP1, 2 and 3, which define the serotype of the produced AAV vector; and the adenovirus helper functions of E2, E4 and VA RNA. The AAV-hC1EI vector (referred to as "AAVrh.10hC1EI") was purified by iodixanol gradient and QHP anion exchange chromatography. Vector genome titers were determined by quantitative TaqMan real-time PCR analysis. A vector coding for an irrelevant protein, AAV-GFP was used as control for the expression studies.

Figure 3B:
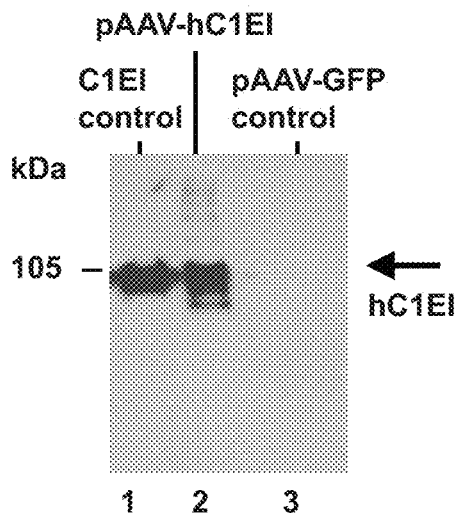
FIG. 3B is an image of a Western blot which depicts expression of hC1E1 encoded by the AAV-hC1EI plasmid in HEK 293T cells.

To assess AAVr.10hC1EI directed expression of the human C1EI protein in vitro, HEK 293T cells were transfected with the AAV-hC1EI plasmid or the control plasmid, and supernatant was harvested 72 hr later. Human C1EI expression in supernatant was evaluated by Coomassie blue stain SDS-PAGE and Western analysis with peroxidase-conjugated goat anti-human kappa light-chain antibody and peroxidase-conjugated anti-human C1EI antibody. As shown in FIG. 3B, human C1EI was detected in cell culture supernatants. The results from this example show the expression of C1EI from an AAV vector.

EXAMPLE 3

This example demonstrates long term in vivo expression of AAVrh.10hC1EI in wild type mice.

To evaluate long-term in vivo serum expression of human C1EI after treatment with the AAVrh.10hC1EI vector, C57Bl/6Albino, C57Bl/6, or SERPING$^{+/-}$ S63 male and female mice at age 6-8 weeks received a single administration of the AAVrh.10hC1EI vector, control AAVrh.10hα1AT vector, or phosphate buffered saline (PBS) at $10^{10}$ or $10^{11}$ genome copies (gc) by intravenous injection in 100 μl volume. Blood from the tail vein was assessed at time 0 and at various time points in the mice until week 20. Blood samples were allowed to clot for 1 hour at 23° C. followed by centrifugation at 13,000 RPM for 10 minutes to collect the serum. Activity of human C1EI was analyzed in each sample.

To evaluate long-term in vivo serum expression of human C1EI in after treatment with the AAV8hC1EI vector, the AAV9hC1EI vector, or the AAVrh.10hC1EI vector, C57Bl/6 male and female wild-type mice at age 6-8 weeks received a single administration of $10^{11}$ genome copies (gc) of either the AAV8hC1EI vector, the AAV9hC1EI vector, the AAVrh.10hC1EI vector, or phosphate buffered saline (PBS) by intravenous injection in 100 μl volume. Blood from the tail vein was assessed at time 0 and at various time points in the mice until week 6. Blood samples were allowed to clot for 1 hour at 23° C. followed by centrifugation at 13,000 RPM for 10 minutes to collect the serum. Activity of human C1EI was analyzed in each sample.

As shown in FIG. 4A, expression of human C1EI was demonstrated for the duration of the experiment (20 weeks), and the activity level of hC1EI was greater than the clinical threshold value at 20 weeks after vector administration (n=5 males/group; n=5 females/group). Additionally, as shown in FIGS. 4B and 4C a dose dependent expression of human C1EI was demonstrated for the duration of the experiment (12 weeks for FIG. 4B and 24 weeks for FIG. 4C), and the activity level of hC1EI was greater than the clinical threshold value in male mice treated with $10^{11}$ or $10^{10}$ gc AAVrh.10hC1EI and female mice treated with $10^{11}$ gc AAVrh.10hC1EI for the duration of the respective experiments (n=5 males/group; n=5 females/group). As shown in FIG. 4D, expression of human C1EI was demonstrated for the duration of the experiment (6 weeks), and the activity level of hC1EI was greater than the clinical threshold value at 6 weeks after vector administration (AAVrh.10hC1EI treated n=3 mice/group; No therapy (PBS control) n=3 males and 1 female).

As shown in FIGS. 5A-5C expression of human C1EI was demonstrated for the duration of the experiment (6 weeks), and the activity level of hC1EI was greater than the clinical threshold value at 6 weeks after either AAV8hC1EI, AAV9hC1EI, or AAVrh.10hC1EI vector administration (n=5 males/group; n=5 females/group). Additionally, as shown in FIG. 5D the activity of human C1EI was similar for each of the vectors tested.

These data demonstrate that each of the AAV8hC1EI, AAV9hC1EI, and AAVrh.10hC1EI vector can provide long-term human C1EI expression from a single administration.

EXAMPLE 4

This example demonstrates the treatment of hereditary angioedema by administering the AAVrh.10hC1EI in the mouse model of hereditary angioedema.

To assess AAVrh.10hC1EI directed expression of hC1EI protein in vivo, S63 (SERPING1$^{+/-}$) mice, age 6 to 8 weeks, were administered a one-time dose of AAVrh.10hC1EI at $10^{11}$ genome copies (gc). Injections were performed intravenously in 100 μl volumes. Blood (100 μl) from the tail vein was assessed at 2 weeks after vector administration. Blood samples were allowed to clot for 1 hr, 23° C., followed by centrifugation at 13,000 RPM for 10 min to collect serum. Activity of hC1EI was measured at 2 weeks in n=4 males and n=4 females. Vector treated (AAVrh.10hC1EI at $10^{11}$ gc) and untreated wild-type B6(Cg)-Tyr$^{c-2J}$/J (Jackson Labs) mice, n=4 males and n=4 females served as controls. At 2 and 6 weeks after vector administration, the mice were administered Evans blue dye (30 mg/kg in 100 μl phosphate buffered saline) by tail vein injection. Photographs of snouts and hind paws were taken 30 min after injection of the Evans blue dye. After the mice were euthanized by $CO_2$ inhalation, hind-paws were removed, blotted dry, and weighed. The Evans blue dye was extracted from equal weights of hind-paws, kidney, intestines, lung, spleen, and heart with 1 ml of formamide overnight at 55° C. and measured spectrophotometrically at 600 nm. Vector treated (AAVrh.10hC1EI at $10^{11}$ gc) and untreated B6(Cg)-Tyr$^{c-2J}$/J (Jackson Labs) mice, served as controls.

The results from these studies indicated that hC1EI activity 2 weeks after AAVrh.10hC1EI gene transfer was greater than the clinical threshold normal value. The same levels of hC1EI activity were observed in B6(Cg)-Tyr$^{c-2J}$/J control mice. No human C1EI activity was detected in serum from mice that were untreated (FIG. 6). Untreated S63 male and female mice had markedly increased vascular permeability compared with the wild-type mice. The blue coloration of the snout and hind-paws was observed within minutes after the Evans Blue dye injection and was much more intense in S63 mice than in the wild-type mice at 2 weeks post vector administration (FIGS. 7A and 7B). Similarly, the blue coloration of the snout and hind-paws was observed within minutes after the Evans Blue dye injection and was much more intense in S63 mice than in the wild-type mice at 6 weeks post vector administration (FIGS. 8A and 8B). Non-treated S63 mice visually exhibited greater extravasation of dye in their hind paws and snouts when compared to the AAVrh.10hC1EI treated group. Dye extravasation was comparable in B6(Cg)-Tyr$^{c-2J}$/J wild-type treated and untreated mice. The quantitative leak phenotype of treated and untreated S63 SERPING1 heterozygous mice was determined by measuring the dye extravasation in major organs (FIGS. 9A-9F). The observed phenotype was validated by spectrophotometric analysis of extracted dye from hind-paws (FIG. 10). Treated mice had significantly ($p<0.001$ males, $p<0.008$ females) lower levels of dye extravasation than their non-treated littermates. These results indicate that treatment of hereditary angioedema with the AAVrh.10hC1EI vector results in a marked reduction of the symptoms of hereditary angioedema.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a deficiency in a functional plasma C1 esterase inhibitor in a mammal, or treating or preventing any symptom thereof, comprising administering a recombinant adeno-associated virus (AAV) vector comprising a promoter operably linked to a nucleic acid sequence that encodes human C1 esterase inhibitor (C1EI) to the mammal, whereupon the nucleic acid is expressed to produce a protein.

2. The method of claim 1, wherein the mammal has hereditary angioedema.

3. The method of claim 2, wherein the method inhibits or reduces submucosal or subcutaneous edema in the mammal.

4. The method of any of claim 3, wherein the composition is administered to the mammal once before and/or after onset of edema.

5. The method of any of claim 3, wherein the composition is administered to the mammal two or more times before and/or after onset of edema.

6. The method of claim 1, wherein the mammal is a human.

7. The method of claim 1, wherein the composition is administered to the mammal by a route of administration selected from the group consisting of intraoral, intramuscular, transdermal, intravenous, intraarterial, subcutaneous, intradermal, and intraperitoneal.

8. The method of claim 1, wherein the AAV vector is a non-human adeno-associated virus.

9. The method of claim 8, wherein the non-human adeno-associated virus is a rhesus macaque adeno-associated virus.

10. The method of claim 9, wherein the rhesus macaque adeno-associated virus is the adeno-associated virus serotype rh.10.

11. The method of claim 1, wherein the promoter is a constitutively active promoter.

12. The method of claim 1, wherein the promoter is a chicken beta-actin promoter.

13. The method of claim 12, wherein the vector further comprises a cytomegalovirus (CMV) enhancer sequence.

14. The method of claim 13, wherein the nucleic acid sequence that encodes human C1EI encodes a polypeptide comprising the amino acid sequence of SEQ ID NO: 1.

* * * * *